United States Patent [19]
Margolin et al.

[11] Patent Number: 6,140,475
[45] Date of Patent: Oct. 31, 2000

[54] CONTROLLED DISSOLUTION CROSSLINKED PROTEIN CRYSTALS

[75] Inventors: Alexey L. Margolin, Newton; Rose A. Persichetti, Stow, both of Mass.; Nancy L. St. Clair, Durham, N.C.; Nazer K. Khalaf, Worcester, Mass.

[73] Assignee: Altus Biologics Inc., Cambridge, Mass.

[21] Appl. No.: 08/834,661

[22] Filed: Apr. 11, 1997

[51] Int. Cl.[7] .......................... C07K 17/00; C12N 11/00; C12N 9/96; A61K 38/00
[52] U.S. Cl. .......................... 530/402; 424/94.1; 435/41; 435/174; 435/188; 435/195; 435/198; 435/219; 435/262.5; 436/518; 510/530; 514/2; 530/810
[58] Field of Search ................................ 435/41, 174, 177, 435/181, 188, 195, 198, 219, 262.5; 424/94.1, 94.6, 94.63; 530/402, 810; 436/518; 510/530; 514/2

[56] References Cited

U.S. PATENT DOCUMENTS

| | | | |
|---|---|---|---|
| 4,373,023 | 2/1983 | Langer et al. | 435/2 |
| 4,579,779 | 4/1986 | Ohno | 428/402.2 |
| 4,606,909 | 8/1986 | Bechgaard et al. | 424/21 |
| 4,760,025 | 7/1988 | Estell et al. | 435/222 |
| 5,066,490 | 11/1991 | Neville, Jr. et al. | 424/85.91 |
| 5,120,650 | 6/1992 | Visuri | 435/176 |
| 5,286,404 | 2/1994 | Eriksen et al. | 252/174.12 |
| 5,385,959 | 1/1995 | Tsaur et al. | 523/201 |
| 5,500,223 | 3/1996 | Behan et al. | 424/451 |
| 5,508,164 | 4/1996 | Kausch et al. | 435/6 |
| 5,569,467 | 10/1996 | Ruiz | 424/489 |
| 5,593,697 | 1/1997 | Barr et al. | 429/490 |
| 5,603,956 | 2/1997 | Mateescu et al. | 424/488 |
| 5,618,710 | 4/1997 | Navia et al. | 435/174 |

FOREIGN PATENT DOCUMENTS

| | | |
|---|---|---|
| 0 341 503 | 11/1989 | European Pat. Off. . |
| WO 89/06279 | 7/1989 | WIPO . |
| WO 92/02617 | 2/1992 | WIPO . |
| WO 98/13119 | 4/1998 | WIPO . |

OTHER PUBLICATIONS

A. Dyer et al. "A Thermal Investigation Of The Stability Of Crystalline Cross–Linked Carboxypeptidase A", *Thermochimica Acta*, vol. 8, pp. 455–464 (1974).

D.J. Haas, "Preliminary Studies On The Denaturation of Cross–Linked Lysozyme Crystals," *Biophysical Journal*, vol. 8, pp. 549–555 (1968).

P.J. Kasvinsky et al. "Activity of Glycogen Phosphorylase in the Crystalline State," *The Journal of Biological Chemistry*, vol. 251, pp. 6852–6859 (1976).

Jim J. Lalonde et al.,"Cross–Linked crystals of *candida rugosa* lipase: highly efficient catalysts for the resolution of chiral esters," *Journal of the American Chemical Society*, vol. 117, pp. 6845–6852 (1995).

K.M. Lee, et al. "Crosslinked Crystaline Horse Liver Alcohol Dehydrogenase as a Redox Catalyst:: Activity and Stability toward Organic Solvent," *Bioorganic Chemistry*, vol. 14, pp. 202–210 (1986).

Alexey L. Margolin, "Novel crystalline catalysts," *Tibtech* vol. 14, pp. 223–230 (1996).

N. L. St. Clair et al. "Crosslinked Enzyme Crystals as Robust Biocatalysts", *Journal of the American Chemical Society*, vol. 114. pp. 7314–7316 (1992).

E. Tuchsen et al. "Kinetic Properties of Subtilisin Type Carlsberg in the Crystalline State," *Carlsberg Research Communications*, vol. 42 pp. 407–420 (1977).

Kui Xu et al., "pH Control of the catalytic activity of cross–linked enzyme crystals in organic solvents", *Journal of the American Chemical Society*, vol. 118, pp. 9815–9819 (1996).

A. Yonath et al. "Crystallographic Studies of Protein Denaturation and Renaturation", *Biochemistry*, vol. 16 pp. 1413–1417 (1977).

Derwent Abstract 88–061232 of Japanese patent application 63017691, published Sep. 1988.

Primary Examiner—David M. Naff
Attorney, Agent, or Firm—Fish & Neave; James F. Haley, Jr.; Margaret A. Pierri

[57] ABSTRACT

Protein crystals crosslinked with a multifunctional crosslinking agent are produced that have the ability to change from an insoluble and stable form to a soluble and active form and to release protein activity at a controlled rate when a change in environment surrounding the crystals occurs. The change in environment may be a change in temperature, pH, chemical composition or shear force acting on the crystals, or a change from a concentrate to a dilute form, or a combination of the changes. The crosslinked protein crystals have a half-life activity under storage conditions greater than at least 2 times that of the soluble protein that is crystallized to form the crystals that are crosslinked, and under conditions of use have an activity similar to the soluble protein. Crosslinking is carried out by reacting a slurry of protein crystals with a multifunctional crosslinking agent such as glutaraldehyde, glyoxal, octanedialdehyde or succinaldehyde using a concentration of crosslinking agent and time for crosslinking that provides crosslinked protein crystals having the desired ability to change due to a change in environment. An epoxide multifunctional crosslinking agent may be used in combination with glutaraldehyde for crosslinking. The crosslinked protein crystals can be used for protein delivery, and may be used in cleaning agents such as detergents, pharmaceutical compositions, vaccines, personal care compositions, veterinary compositions, foods, feeds, diagnostics and decontamination formulations. Proteins used include enzymes and therapeutic or prophylactic proteins such as hormones and antibodies.

19 Claims, 9 Drawing Sheets

CONTROLLED DISSOLUTION CROSSLINKED PROTEIN CRYSTALS

TECHNICAL FIELD OF THE INVENTION

The present invention relates to crosslinked protein crystals characterized by the ability to change from insoluble and stable form to soluble and active form upon a change in the environment surrounding said crystals, said change being selected from the group consisting of change in temperature, change in pH, change in chemical composition, change from concentrate to dilute form, change in shear force acting upon the crystals and combinations thereof. According to one embodiment of this invention, such crosslinked protein crystals are capable of releasing their protein activity at a controlled rate. This invention also provides methods for producing such crosslinked protein crystals, methods using them for protein delivery and methods using them in cleaning agents, including detergents, pharmaceutical compositions, vaccines, personal care compositions, including cosmetics, veterinary compositions, foods, feeds, diagnostics and formulations for decontamination.

BACKGROUND OF THE INVENTION

Proteins are used in a wide range of applications in the fields of industrial chemistry, pharmaceuticals, veterinary products, cosmetics and other consumer products, foods, feeds, diagnostics and decontamination. At times, such uses have been limited by constraints inherent in proteins themselves or imposed by the environment or media in which they are used. Such constraints may result in poor stability of the proteins, variability of performance or high cost. In order for proteins to realize their full potential in the fields in which they are used, they must be able to function without excessive intervention by their surrounding environment. In the past, environmental elements have often posed barriers to the widespread use of proteins.

Various approaches have been employed to overcome these barriers. However, these approaches have incurred either loss of protein activity or the additional expense of protein stabilizing carriers or formulations.

One unique approach to overcoming barriers to the widespread use of proteins is crosslinked enzyme crystal ("CLEC™") technology [N. L. St. Clair and M. A. Navia, *J. Am. Chem. Soc.*, 114, pp. 4314–16 (1992)]. Crosslinked enzyme crystals retain their activity in environments that are normally incompatible with enzyme function. Such environments include prolonged exposure to proteases and other protein digestion agents, high temperature or extreme pH. In such environments, crosslinked enzyme crystals remain insoluble and stable.

Protein solubility, leading to controlled release or dissolution of protein, is important in many industrial fields. Such industries include those concerning cleaning agents, including detergents, pharmaceuticals, consumer and personal care products, veterinary products, foods, feeds, diagnostics and decontamination. Various approaches to controlled release have been proposed. These include encapsulation, such as that described in U.S. Pat. Nos. 4,579,779 and 5,500,223. Other approaches include the use of mechanical or electrical feed devices and osmotic pumps.

Controlled release in the pharmaceutical field has been addressed by various means. U.S. Pat. No. 5,569,467 refers to the use of sustained release microparticles comprising a biocompatible polymer and a pharmaceutical agent, which is released as the polymer degrades. U.S. Pat. No. 5,603,956 refers to solid, slow release pharmaceutical dosage units comprising crosslinked amylase, alpha amylase and a pharmaceutical agent. U.S. Pat. No. 4,606,909 refers to oral, controlled-release multiple unit formulations in which homogeneous cores containing particles of sparingly soluble active ingredients are coated with a pH-sensitive erodable coating. U.S. Pat. No. 5,593,697 refers to pharmaceutical or veterinary implants comprising a biologically active material, an excipient comprising at least one water soluble material and at least one water insoluble material and a polymer film coating adapted to rupture at a predetermined period of time after implant.

The objective of controlled release of proteins, however, must be balanced with the fact that the protein itself may not be stable under storage conditions. Protein stability may also be adversely affected by other components of the formulation in which it is contained. For example, heavy duty liquid detergents constitute hostile environments for component enzymes. Such problems have been approached through the use of mutant subtilisin proteases, which are said to have improved oxidative stability. See U.S. Pat. No. 4,760,025 and PCT patent application WO89/06279. Proteins, the enzymes most widely used in detergents, catalyze their own decomposition. Strategies such as the addition of protease inhibitors (e.g., borate with glycols) or the lowering of water activity have been only partially effective.

Another approach, described in U.S. Pat. No. 5,385,959, is encapsulation of degradation-sensitive detergent components in capsules of composite emulsion polymers, which permit dilution release thereof. U.S. Pat. No. 5,286,404 refers to a liquid detergent composition said to have improved enzyme solubility while preserving enzyme activity. The improvement is attributed to chemical modification of free primary amino groups in an enzyme solution via aldehyde treatment, acylation or alkylation.

Despite such progress in protein technology generally, the need still exists for proteins which are stable under conditions of storage, while active under conditions of use.

DISCLOSURE OF THE INVENTION

The present invention relates to crosslinked protein crystals characterized by the ability to change from insoluble and stable form to soluble and active form upon a change in the environment surrounding said crystals, said change being selected from the group consisting of change in temperature, change in pH, change in chemical composition, change from concentrate to dilute form, change in shear force acting upon the crystals and combinations thereof. According to one embodiment of this invention, such crosslinked protein crystals are capable of releasing their protein activity at a controlled rate.

Advantageously, the crosslinked protein crystals of this invention are insoluble and stable under storage conditions and soluble and active under conditions of use.

This invention also provides cleaning agents, including detergents, pharmaceutical compositions, vaccines, personal care compositions, including cosmetics, veterinary compositions, foods, feeds, diagnostics and formulations for decontamination. Additionally, this invention includes methods for producing such crosslinked protein crystals and methods for protein delivery using them.

DETAILED DESCRIPTION OF THE INVENTION

Figure 1:
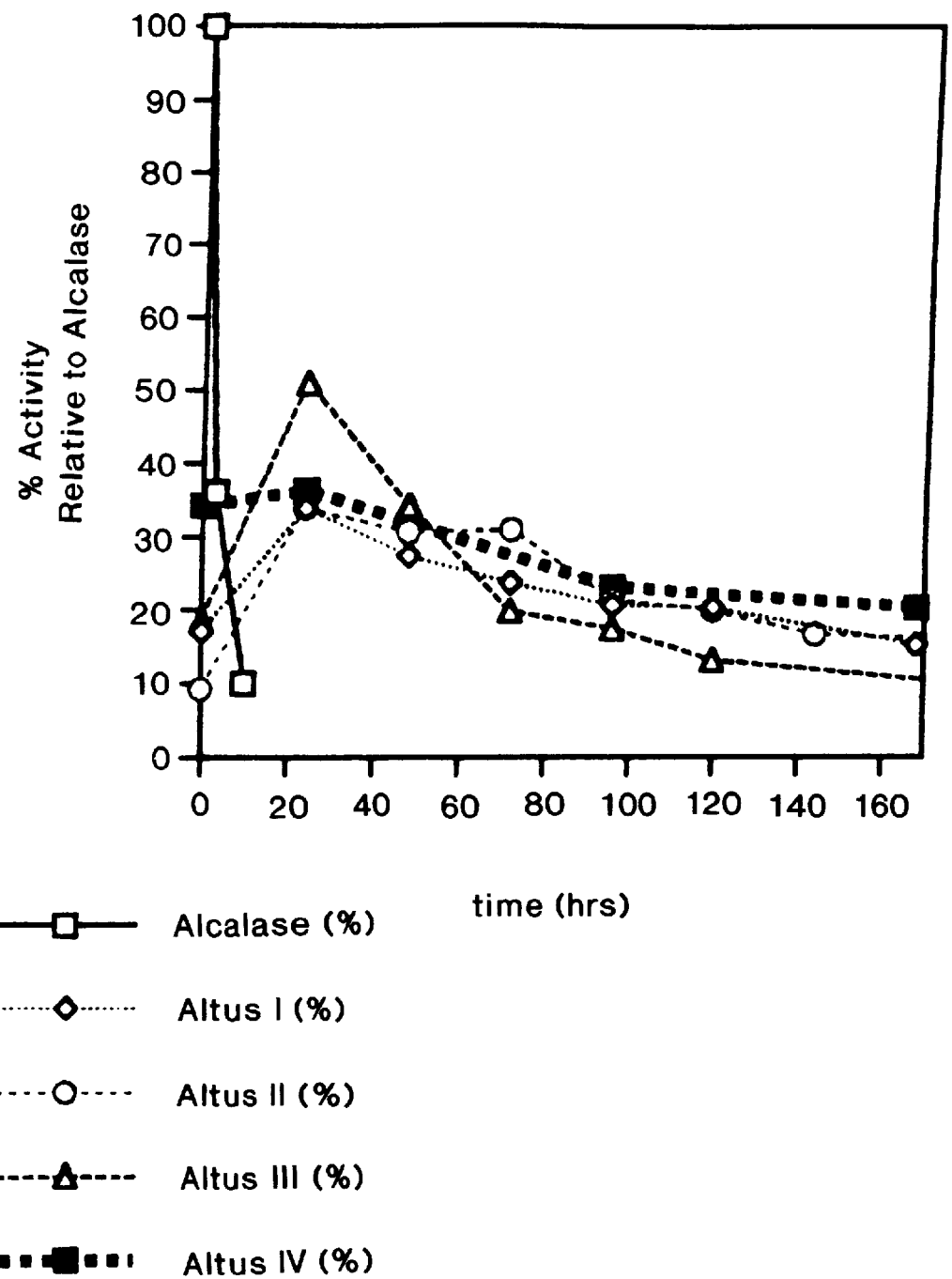
FIG. 1 is a graph representing the stability of various enzymes in Ciba detergent #16 at 40° C.

In order that the invention herein described may be more fully understood, the following detailed description is set forth. In the description, the following terms or phrases are employed:

Aqueous-organic solvent mixture—a mixture comprising n % organic solvent, where n is between 1 and 99 and m % aqueous, where m is 100-n.

Catalytically effective amount—an amount of crosslinked protein crystals of this invention which is effective to treat, protect, repair or detoxify the area to which they are applied over some period of time.

Change in chemical composition—any change in the chemical components of the environment surrounding the crosslinked protein crystals that affects the environment or the crosslinker, including addition of chemical reagents, chemical changes induced by application of energy in the form of light, microwave, or radiation to the environment, chemical events that affect the crosslinker and combinations thereof.

Change in shear force acting upon the crystals—any change in factors of the environment surrounding the crosslinked protein crystals under conditions of use, such as, changes in mechanical pressure, both positive and negative, revolution stirring, centrifugation, tumbling, mechanical agitation and filtration pumping.

Controlled dissolution—dissolution of crosslinked protein crystals or release of the protein constituent of said crystals that is (1) triggered by a change in the environment surrounding said crystals, said change being selected from the group consisting of change in temperature, change in pH, change in chemical composition, change from concentrate to dilute form, change in shear force acting upon the crystals and combinations thereof and (2) controlled by a factor selected from the group consisting of the degree of crosslinking of said crosslinked protein crystals, the length of time of exposure of protein crystals to the crosslinking agent, the rate of addition of crosslinking agent to said protein crystals, the nature of the crosslinker, the chain length of the crosslinker, the surface area of said crosslinked protein crystals, the size of said crosslinked protein crystals, the shape of said crosslinked protein crystals and combinations thereof. As used herein, the phrase "controlled dissolution" does not include leaching.

Formulations for decontamination—formulations selected from the group consisting of: formulations for decontamination of chemical wastes, herbicides, insecticides, pesticides, environmental hazards and chemical warfare agents.

Insoluble and stable form of a protein—a form of a protein which is insoluble in aqueous solvents, organic solvents or aqueous-organic solvent mixtures and which displays greater stability than the soluble form of the protein. According to an alternate embodiment of this invention, the phrase "insoluble and stable form of a protein" may be a protein which is insoluble in dry formulations but soluble in wet formulations. In any embodiment, the crosslinked protein crystals may be active in insoluble form. And in one embodiment, the crosslinked protein crystals may be active in insoluble form, then dissolve or are removed or digested once their function is complete.

Organic solvents—any solvent of non-aqueous origin.

Pharmaceutically effective amount—an amount of crosslinked protein crystals which is effective to treat a condition in an individual to whom they are administered over some period of time.

Prophylactically effective amount—an amount of crosslinked protein crystals which is effective to prevent a condition in an individual to whom they are administered over some period of time.

Protein—any peptide having a tertiary structure or any protein.

Protein activity—an activity selected from the group consisting of binding, catalysis, activities which generate a functional response within the environment in which the protein used, such as induction of immune response and immunogenicity, or combinations thereof.

Protein activity release rate—the quantity of protein dissolved per unit time.

The crosslinked protein crystals of this invention are particularly advantageous because they are stable in harsh environments imposed by the formulations or compositions in which they are employed or conditions of their storage. At the same time, these crosslinked protein crystals are capable of (1) change to soluble and active form (an active form including, in one embodiment of this invention, a form which is active against macromolecular substrates) or (2) controlled dissolution or release of their activity when exposed to one or more triggers in their environment. Such triggers may be selected from the group consisting of change in temperature, change in pH, change in chemical composition, change from concentrate to dilute form, change in shear force acting upon the crystals and combinations thereof. Controlled dissolution or release of activity of crosslinked protein crystals according to this invention may also be triggered over a change in time.

Specific examples of such triggers include an increase or decrease in temperature, for example, an increase in temperature from a low temperature between about 0° C. and about 20° C. to a high temperature between about 25° C. and about 70° C. Other triggers include a change from acidic pH to basic pH and a change from basic pH to acidic pH. Examples of triggers of change from concentrate to dilute form include, for example, a change in solute concentration, a change in concentration of all solutes from about 2-fold to about 10,000-fold, a change in concentration of all solutes from about 2-fold to about 700-fold, an increase or decrease in salt concentration, an increase or decrease in water concentration, an increase or decrease in organic solvent concentration, a decrease in protein concentration and a decrease in detergent concentration.

Additional triggers involve changes in chemical composition of the environment surrounding the crosslinked protein crystals that affect the environment or the crosslinker itself. Such changes include, for example, addition of chemical reagents, increase or decrease in organic solvent concentration, chemical events that affect the crosslinker, chemical changes induced by application of energy, including light, microwave or radiation. As explained above, any of these triggers may act in combination or in sequence with one or more of the other triggers.

Controlled dissolution of crosslinked protein crystals according to the present invention may also be effected by a change in time sufficient to permit a protein activity release rate between about 0.1% per day and about 100% per day, a change in time sufficient to permit a protein activity release rate between about 0.01% per hour and about 100% per hour and a change in time sufficient to permit a protein activity release rate between about 1% per minute and about 50% per minute.

Crosslinked protein crystals according to this invention, therefore, include those capable of releasing their protein activity at a controlled rate upon exposure to a change in their environment, said change being selected from the group consisting of change in pH, change in solute concentration, change in temperature, change in chemical composition, change in shear force acting upon the crystals and combinations thereof. Said controlled rate of releasing protein activity may be determined by a factor selected from the group consisting of the degree of crosslinking of the crosslinked protein crystals, the length of time of exposure of protein crystals to the crosslinking agent, the rate of addition of crosslinking agent to the protein crystals, the nature of the crosslinker, the chain length of the crosslinker, the surface area of the crosslinked protein crystals, the size of the crosslinked protein crystals, the shape of the crosslinked protein crystals and combinations thereof.

As a result of their crystalline nature, the crosslinked protein crystals of this invention achieve uniformity across the entire crosslinked crystal volume. This uniformity is maintained by the intermolecular contacts and chemical crosslinks between the protein molecules constituting the crystal lattice. The protein molecules maintain a uniform distance from each other, forming well-defined stable pores within the crosslinked protein crystals that facilitate access of substrate to the protein, as well as removal of product. In these crosslinked protein crystals, the lattice interactions, when fixed by chemical crosslinks, are particularly important in providing stability and preventing denaturation, especially in storage, under conditions including harsh environments created by components of compositions in which the crystals are used. At the same time, the protein crystals are crosslinked in such a way that they dissolve or release their protein activity upon exposure to a trigger in their environment encountered under conditions of use. Thus, they may be substantially insoluble and stable in a composition under storage conditions and substantially soluble and active under conditions of use of said composition.

Factors contributing to the release rate of protein activity of crosslinked protein crystals according to this invention include the degree of crosslinking of the crosslinked protein crystals, the length of time of exposure of protein crystals to the crosslinking agent, the rate of addition of crosslinking agent to the protein crystals, the length of time of exposure of protein crystals to the crosslinking agent, the nature of the crosslinker, the chain length of the crosslinker, the surface area of the crosslinked protein crystals, the size of the crosslinked protein crystals, the shape of the crosslinked protein crystals and combinations thereof.

In addition to their activity, crosslinked protein crystals according to this invention are particularly stable and insoluble under storage conditions, including the attendant storage temperature, storage pH, storage time, storage concentrate form, storage involving little or no shear force acting upon the crystals, or combinations thereof. Advantageously, these crosslinked protein crystals are soluble and active under conditions of use, including conditions involving change in temperature, change in pH, change in chemical composition, change from concentrate to dilute form, change in shear force acting upon the crystals and combinations thereof. Such properties make the crosslinked protein crystals of this invention particularly useful for delivery of cleaning agents, including detergents, pharmaceuticals, personal care agents or compositions, including cosmetics, vaccines, veterinary compositions, foods, feeds, diagnostics and formulations for decontamination.

According to one embodiment, the crosslinked protein crystals of this invention are characterized by a half-life of activity under storage conditions which is greater than at least 2 times that of the soluble form of the protein that is crystallized to form the crystals that are crosslinked and activity similar to that of the soluble form of the protein under conditions of use.

The protein constituent of the crosslinked protein crystals of this invention may be any protein, including, for example, therapeutic proteins, prophylactic proteins, including antibodies, cleaning agent proteins, including detergent proteins, personal care proteins, including cosmetic proteins, veterinary proteins, food proteins, feed proteins, diagnostic proteins and decontamination proteins. Included among such proteins are enzymes, such as, for example, hydrolases, isomerases, lyases, ligases, transferases and oxidoreductases. Examples of hydrolases include thermolysin, elastase, esterase, lipase, nitrilase, amylase, pectinase, subtilinase, hydantoinase, asparaginase, urease, subtilisin and other proteases and lysozyme. Examples of lyases include aldolases and hydroxynitrile lyase. Examples of oxidoreductases include peroxidase, laccase, glucose oxidase, alcohol dehydrogenase and other dehydrogenases. Other enzymes which may be crystallized and crosslinked include cellulases and oxidases.

Examples of therapeutic or prophylactic proteins include hormones, antibodies, inhibitors, growth factors, trophic factors, cytokines, lymphokines, toxoids, erythropoietin, Factor VIII, insulin, amylin, TPA, dornase-$\alpha$, $\alpha$-1-antitripsin, human growth hormones, nerve growth hormones, bone morphogenic proteins, urease, toxoids, fertility hormones, FSH, LSH, postridical hormones, tetanus toxoid, diptheria toxoid, vitamins and nutrients.

According to one embodiment of this invention, crosslinked protein crystals are characterized by activity which is similar to that of their soluble or uncrosslinked crystallized counterparts under conditions of use. Advantageously however, the crosslinked protein crystals of this invention display improved stability under storage conditions, as compared to their soluble or uncrosslinked crystallized counterpart proteins.

The crosslinked protein crystals of this invention may be used in any of a number of chemical processes. Such processes include industrial and research-scale processes, such as organic synthesis of specialty chemicals and pharmaceuticals. Enzymatic conversion processes include oxidations, reductions, additions, including esterifications and transesterifications, hydrolyses, eliminations, rearrangements, and asymmetric conversions, including stereoselective, stereospecific and regioselective reactions.

Thus, crosslinked protein crystals according to this invention may be advantageously used instead of conventional soluble or immobilized proteins in cleaning agents, including detergents, pharmaceuticals, veterinary compounds, personal care compositions, including cosmetics, foods, feeds, vaccines, pulp, paper and textile processing, diagnostics and formulations for decontamination.

Crosslinked protein crystals according to this invention may also be used in various environmental applications. They may be used in place of conventional soluble or immobilized proteins for environmental purposes, such wide area as decontamination of environmental hazards.

Alternatively, the crosslinked protein crystals of this invention may be used in cleaning agents, selected from the group consisting of detergents, such as powdered detergents and liquid detergents, bleaches, household cleaners, hard surface cleaners, industrial cleaners and carpet and upholstery shampoos.

Cleaning agents containing crosslinked protein crystals according to the present invention may also comprise compounds conventionally included in such agents. See, for example, *Soaps and Detergents, A Theoretical and Practical Review*, Louis Spitz (Ed.), AOCS Press (Champlain, Ill.) (1996). Such compounds include anionic, non-ionic, cationic or zwitterionic surfactants, or mixtures thereof.

Anionic surfactants are exemplified by alkyl sulfates, alkyl ether sulfates, alkyl sulfonates, alkylaryl sulfonates, olefin sulfonates, alkyl ether phosphates, alkyl ether phosphates, fatty acid salts, soaps, isothionates and sulfonated unsaturated esters and acids.

Non-ionic surfactants are exemplified by products of condensation of an organic aliphatic or alkyl aromatic hydrophobic compound with an alkylene oxide, alkyl polyglucosides and sugar esters.

Cationic surfactants are exemplified by quarternary ammonium salts of tertiary alkyl amines, amino amides, amino esters or imidazolines containing al least one long chain ($C_8$–$C_{22}$) aliphatic group or an alkyl-aryl group, wherein alkyl comprises about 4 to 12 carbon atoms and aryl is preferably a phenylene group.

Zwitterionic surfactants are exemplified by derivatives of quarternary ammonium, quarternary phosphonium or tertiary sulfonium compounds, derivatives of secondary and tertiary amines and derivatives of heterocyclic secondary and tertiary amines.

And crosslinked protein crystals according to this invention may be used as ingredients in personal care compositions, including cosmetics, such as creams, lotions, emulsions, foams, washes, compacts, gels, mousses, slurries, powders, sprays, pastes, ointments, salves, balms, drops, shampoos, and sunscreens. In topical creams and lotions, for example, they may be used as humectants or for skin protection, softening, bleaching, cleaning, deproteinization, lipid removal, moisturizing, decoloration, coloration or detoxification. They may also be used as anti-oxidants in cosmetics.

According to this invention, any individual, including humans and other mammals, may be treated in a pharmaceutically acceptable manner with a pharmaceutically effective or a catalytically effective amount of crosslinked protein crystals for a period of time sufficient to treat a condition in the individual to whom they are administered over some period of time. Alternatively, individuals may receive a prophylactically effective or a catalytically effective amount of crosslinked protein crystals of this invention which is effective to prevent a condition in the individual to whom they are administered over some period of time.

Such crosslinked protein crystals may be administered alone, as part of a pharmaceutical, personal care or veterinary preparation or as part of a prophylactic preparation, such as a vaccine, with or without adjuvant. They may be administered by parenteral or non-parenteral route. For example, they may be administered by oral, pulmonary, nasal, aural, anal, dermal, ocular, intravenous, intramuscular, intraarterial, intraperitoneal, mucosal, sublingual, subcutaneous, or intracranial route. In either pharmaceutical, personal care or veterinary applications, crosslinked protein crystals may be topically administered to any epithelial surface. Such epithelial surfaces include oral, ocular, aural, anal and nasal surfaces, to treat, protect, repair or detoxify the area to which they are applied.

The present invention also includes controlled release formulations comprising crosslinked protein crystals according to this invention. In such formulations, the crosslinked protein crystals are substantially insoluble under storage conditions and capable of releasing their protein activity in vivo at a controlled rate. For example, a pharmaceutical controlled release formulation according to this invention, administered by oral route, is characterized in that the component crosslinked protein crystals are substantially insoluble under gastric pH conditions and substantially soluble under small intestine pH conditions. Alternatively, for these and other uses according to this invention, the crosslinked protein crystals may be active in the insoluble form and then dissolve and are removed or digested once their function is complete.

Pharmaceutical, personal care, veterinary or prophylactic compositions comprising crosslinked protein crystals according to this invention may also be selected from the group consisting of tablets, liposomes, granules, spheres, microparticles, microspheres and capsules.

For such uses, as well as other uses according to this invention, crosslinked protein crystals may be formulated into tablets. Such tablets constitute a liquid-free, dust-free form of crosslinked protein crystal storage which are easily handled and retain acceptable levels of activity.

Alternatively, the crosslinked protein crystals may be in a variety of conventional depot forms employed for administration to provide reactive compositions. These include, for example, solid, semi-solid and liquid dosage forms, such as liquid solutions or suspensions, gels, creams, balms, emulsions, lotions, slurries, powders, sprays, foams, pastes, ointments, salves, balms and drops.

Compositions or formulations comprising the crosslinked protein crystals of this invention may also comprise any conventional carrier or adjuvant used in pharmaceuticals, personal care compositions or veterinary formulations. These carriers and adjuvants include, for example, Freund's adjuvant, ion exchangers, alumina, aluminum stearate, lecithin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, sodium chloride, zinc salts, colloidal silica, magnesium, trisilicate, cellulose-based substances and polyethylene glycol. Adjuvants for topical or gel base forms may include, for example, sodium carboxymethylcellulose, polyacrylates, polyoxyethylene-polyoxypropylene-block polymers, polyethylene glycol and wood wax alcohols.

According to one embodiment of this invention, crosslinked protein crystals may be combined with any conventional materials used for controlled release administration. Such materials include, for example, coatings, shells and films, such as enteric coatings and polymer coatings and films.

The most effective mode of administration and dosage regimen of formulations or compositions comprising crosslinked protein crystals of this invention will depend on the effect desired, previous therapy, if any, the individual's health status or status of the condition itself and response to the crosslinked protein crystals and the judgment of the treating physician or clinician. The crosslinked protein crystals may be administered in any dosage form acceptable for pharmaceuticals, personal care compositions or veterinary formulations, at one time or over a series of treatments.

The amount of the crosslinked protein crystals that may be combined with carrier materials to produce a single dosage form will vary depending upon the particular mode of administration, formulation, dose level or dose frequency. A typical preparation will contain between about 0.01% and about 99%, preferably between about 1% and about 50%, crosslinked protein crystals (w/w).

Upon improvement of the individual's condition, a maintenance dose of crosslinked protein crystals may be administered, if necessary. Subsequently, the dosage or frequency of administration, or both, may be reduced as a function of the symptoms, to a level at which the improved condition is retained. When the condition has been alleviated to the desired level, treatment should cease. Individuals may, however, require intermittent treatment on a long-term basis upon any recurrence of the condition or symptoms thereof.

An alternate embodiment of the present invention includes protein delivery systems comprising the crosslinked protein crystals disclosed herein. Such a system may be used to deliver proteins such as those included in cleaning agents, such as detergents, personal care products, such as cosmetics, pharmaceuticals, veterinary compositions, vaccines, foods, feeds, diagnostics and formulations for decontamination. Protein delivery systems of this invention, which may be formulations or devices, such as implantable devices, may be microparticulate protein delivery systems, wherein the crosslinked protein crystals have a longest dimension between about 0.01 $\mu$m and about 500 $\mu$m, alternatively between about 0.1 $\mu$m and about 50 $\mu$m. The crosslinked protein crystal components of such systems may have a shape selected from the group consisting of: spheres, needles, rods, plates, such as hexagons and squares, rhomboids, cubes, bipryamids and prisms. Advantageously, the crosslinked crystal form of the proteins of this invention allow loading of up to between about 50% and about 90% protein per unit of weight.

One example of a protected protein system according to this invention is suitable for storage in a medium such as a liquid detergent, prior to use. The crosslinked protein crystal components of such a system are insoluble under storage conditions in said medium—which typically causes degradation of the soluble form of the protein that is crystallized to form said crystal that is crosslinked—and soluble under conditions of use.

According to the present invention, preparation of crosslinked protein crystals includes the steps of crystallizing and crosslinking the protein. This may be carried out as illustrated below.

Preparation of Crosslinked Protein Crystals—Protein Crystallization

Protein crystals are grown by controlled crystallization of protein out of aqueous solution or aqueous solution-containing organic solvents. Conditions to be controlled include, for example, the rate of evaporation of solvent, the presence of appropriate co-solutes and buffers, pH and temperature. A comprehensive review of the various factors affecting the crystallization of proteins has been published by McPherson, *Methods Enzymol.*, 114, pp. 112–20 (1985).

McPherson and Gilliland, *J. Crystal Growth*, 90, pp. 51–59 (1988) have compiled comprehensive lists of proteins and nucleic acids that have been crystallized, as well as the conditions under which they were crystallized. A compendium of crystals and crystallization recipes, as well as a repository of coordinates of solved protein and nucleic acid structures, is maintained by the Protein Data Bank at the Brookhaven National Laboratory [http//www. pdb.bnl.gov; Bernstein et al., *J. Mol. Biol.*, 112, pp. 535–42 (1977)]. These references can be used to determine the conditions necessary for crystallization of a protein, as a prelude to the formation of an appropriate crosslinked protein crystal, and can guide the crystallization strategy for other proteins. Alternatively, an intelligent trial and error search strategy can, in most instances, produce suitable crystallization conditions for many proteins, provided that an acceptable level of purity can be achieved for them [see, e.g., C. W. Carter, Jr. and C. W. Carter, *J. Biol. Chem.*, 254, pp. 12219–23 (1979)].

For use in crosslinked protein crystals according to this invention, the large single crystals which are needed for X-ray diffraction analysis are not required. Microcrystalline showers are suitable.

For example, the crosslinked protein crystals may have a longest dimension between about 0.01 $\mu$m and about 500 $\mu$m, alternatively, between 0.1 $\mu$m and about 50 $\mu$m. They may also have a shape selected from the group consisting of: spheres, needles, rods, plates, such as hexagons and squares, rhomboids, cubes, bipryamids and prisms.

In general, crystals are produced by combining the protein to be crystallized with an appropriate aqueous solvent or aqueous solvent containing appropriate crystallization agents, such as salts or organic solvents. The solvent is combined with the protein and subjected to agitation at a temperature determined experimentally to be appropriate for the induction of crystallization and acceptable for the maintenance of protein activity and stability. The solvent can optionally include co-solutes, such as divalent cations, co-factors or chaotropes, as well as buffer species to control pH. The need for co-solutes and their concentrations are determined experimentally to facilitate crystallization. In an industrial-scale process, the controlled precipitation leading to crystallization can best be carried out by the simple combination of protein, precipitant, co-solutes and, optionally, buffers in a batch process. Alternative laboratory crystallization methods, such as dialysis or vapor diffusion, can also be adopted. McPherson, supra and Gilliland, supra, include a comprehensive list of suitable conditions in their reviews of the crystallization literature. Occasionally, incompatibility between the crosslinking agent and the crystallization medium might require exchanging the crystals into a more suitable solvent system.

Many of the proteins for which crystallization conditions have already been described, may be used to prepare crosslinked protein crystals according to this invention. It should be noted, however, that the conditions reported in most of the above-cited references have been optimized to yield, in most instances, a few large, diffraction quality crystals. Accordingly, it will be appreciated by those of skill in the art that some degree of adjustment of these conditions to provide a high yielding process for the large scale production of the smaller crystals used in making crosslinked protein crystals may be necessary.

Preparation of Crosslinked Protein Crystals—Crosslinking of Protein Crystals

Once protein crystals have been grown in a suitable medium they can be crosslinked. Crosslinking results in stabilization of the crystal lattice by introducing covalent links between the constituent protein molecules of the crystal. This makes possible transfer of the protein into an alternate environment that might otherwise be incompatible with the existence of the crystal lattice or even with the existence of intact protein.

Advantageously, crosslinking according to the present invention is carried out in such a way that, under conditions of storage, the crosslinking interactions prevent the constituent protein molecules in the crystal from going back into solution, effectively insolubilizing or immobilizing the protein molecules into microcrystalline particles. Upon exposure to a trigger in the environment surrounding the crosslinked protein crystals, such as under conditions of use rather than storage, the protein molecules dissolve, releasing their protein activity. The rate of dissolution is controlled by one or more of the following factors: the degree of crosslinking, the length of time of exposure of protein crystals to the crosslinking agent, the rate of addition of crosslinking agent to the protein crystals, the nature of the crosslinker, the chain length of the crosslinker, the surface area of the crosslinked protein crystals, the size of the crosslinked protein crystals, the shape of the crosslinked protein crystals and combinations thereof.

Crosslinking can be achieved using one or a combination of a wide variety of multifunctional reagents, at the same time (in parallel) or in sequence, including bifunctional reagents. Upon exposure to a trigger in the surrounding environment, or over a given period of time, the crosslinks between protein crystals crosslinked with such multifunctional crosslinking agents lessen or weaken, leading to protein dissolution or release of activity. Alternatively, the crosslinks may break at the point of attachment, leading to protein dissolution or release of activity. Such crosslinking agents include glutaraldehyde, succinaldehyde, octanedialdehyde and glyoxal. Additional multifunctional crosslinking agents include halo-triazines, e.g., cyanuric chloride; halo-pyrimidines, e.g., 2,4,6-trichloro/bromo-pyrimidine; anhydrides or halides of aliphatic or aromatic mono- or di-carboxylic acids, e.g., maleic anhydride, (meth)acryloyl chloride, chloroacetyl chloride; N-methylol compounds, e.g., N-methylol-chloro acetamide; di-isocyanates or di-isothiocyanates, e.g., phenylene-1,4-di-isocyanate and aziridines. Other crosslinking agents include epoxides, such as, for example, di-epoxides, tri-epoxides and tetra-epoxides. According to a preferred embodiment of this invention, the crosslinking agent is glutaraldehyde, used alone or in sequence with an epoxide. For a representative listing of other available crosslinking reagents see, for example, the 1996 catalog of the Pierce Chemical Company. Such multifunctional crosslinking agents may also be used, at the same time (in parallel) or in sequence, with reversible crosslinking agents, such as those described below.

According to an alternate embodiment of this invention, crosslinking may be carried out using reversible crosslinkers, in parallel or in sequence. The resulting crosslinked protein crystals are characterized by a reactive multi-functional linker, into which a trigger is incorporated as a separate group. The reactive functionality is involved in linking together reactive amino acid side chains in a protein and the trigger consists of a bond that can be broken by altering one or more conditions in the surrounding environment (e.g., pH, temperature, or thermodynamic water activity). This is illustrated diagrammatically as:

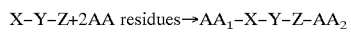

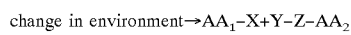

where X and Z are groups with reactive functionality where Y is a trigger where $AA_1$ and $AA_2$ represent reactive amino acid residues on the same protein or on two different proteins. The bond between the crosslinking agent and the protein may be a covalent or ionic bond, or a hydrogen bond. The change in surrounding environment results in breaking of the trigger bond and dissolution of the protein. Thus, the crosslinks between protein crystals crosslinked with such reversible crosslinking agents break, leading to protein crystal dissolution or release of activity.

Alternatively, the reactive functionality of the crosslinker and the trigger may be the same, as in:

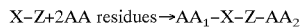

The crosslinker may be homofunctional (X=Y) or heterofunctional (X is not equal to Y). The reactive functionality X and Y may be, but not limited to the following functional groups (where R, R', R", and R'" may be alkyl, aryl or hydrogen groups):

I. Reactive acyl donors are exemplified by: carboxylate esters RCOOR', amides RCONHR', Acyl azides $RCON_3$, carbodiimides R—N=C=N—R', N-hydroxyimide esters, RCO—O—NR', imidoesters R—C=$NH2^+$(OR'), anhydrides RCO—O—COR', carbonates RO—CO—O—R', urethanes RNHCONHR', acid halides RCOHal (where Hal=a halogen), acyl hydrazides RCONNR'R", O-acylisoureas RCO—O—C=NR'(—NR"R'"), II. Reactive carbonyl groups are exemplified by: aldehydes RCHO and ketones RCOR', acetals $RCO(H_2)R'$, ketals $RR'CO_2R'R''$. Reactive carbonyl containing functional groups known to those well skilled in the art of protein immobilization and crosslinking are described in the literature [*Pierce Catalog and Handbook*, Pierce Chemical Company, Rockford, Ill. (1994); S. S. Wong, *Chemistry of Protein Conjugation and Cross-Linking*, CRC Press, Boca Raton, Fla. (1991)].

III. Alkyl or aryl donors are exemplified by: alkyl or aryl halides R-Hal, azides R—$N_3$, sulfate esters $RSO_3R'$, phosphate esters $RPO(OR'_3)$, alkyloxonium salts $R_3O+$, sulfonium $R_3S+$, nitrate esters $RONO_2$, Michael acceptors $RCR'=CR'''COR''$, aryl fluorides $ArF$, isonitriles $RN+\equiv C—$, haloamines $R_2N$-Hal, alkenes and alkynes.

IV. Sulfur containing groups are exemplified by disulfides RSSR', sulfhydryls RSH, epoxides $R_2C^OCR'_2$.

V. Salts are exemplified by alkyl or aryl ammonium salts $R_4N+$, carboxylate RCOO—, sulfate $ROSO_3$—, phosphate $ROPO_3"$ and amines $R_3N$.

The table below includes examples of triggers, organized by release mechanism. In the table, R= is a multifunctional crosslinking agent that can be an alkyl, aryl, or other chains with activating groups that can react with the protein to be crosslinked. Those reactive groups can be any variety of groups such as those susceptible to nucleophilic, free radical or electrophilic displacement including halides, aldehydes, carbonates, urethanes, xanthanes, epoxides among others.

| Trigger | Examples | Release Conditions |
|---|---|---|
| 1. Acid Labile Linkers | R—O—R e.g. Thp, MOM, Acetal, ketal Aldol, Michael adducts, esters | $H^+$ or Lewis Acidic catalysts |
| 2. Base Labile Linkers | R'OCO2—R' Carbonates R'O—$CONR_2$ Carbamates $R_2$'$NCONR_2$ Urethanes Aldol, Michael adducts, esters | Variety of basic media |
| 3. Fluoride Labile Linkers | R—$OSiR_3$ Various Si containing linkers | Aqueous $F^-$ |
| 4. Enzyme Labile Linkers | RCOOR, $RCONR_2$' | Free lipases, amidases, esterases |
| 5. Reduction Labile Linkers | Disulfide linkers that cleave via Hydrogenolysis Reductive Elimination R'—S—S—R | $H_2$ catalyst; Hydrides |
| 6. Oxidation Labile Linkers | R—$OSiR_3$ Glycols R— CH(OH)—CH(OH)—R' | Oxidizing agents: e.g. $H_2O_2$, NaOCl, $IO_4^-$ Metal based oxidizers, other hypervalent oxidents |
| 7. Thio-labile linkers | R'—S—S—R | Thiols, e.g., Cys, DTT, mercaptoethanol |
| 8. Heavy Metal Labile Linkers | Various Allyl Ethers $ROCH_2CH=CHR$ Alkyl, Acyl Allyl ester | Transition metal based reagents (Pd, Ir, Hg, Ag, Cu, Tl, Rh) Pd(0) catalysts |
| 9. Photolabile Linkers | O-nitrobenzyl (ONB) DESYL groups in linker | light (hv) |
| 10. Free Radical Labile Linkers | Thiohydroxa- mate ester (Barton ester) | Free radical initiator |
| 11. Metal- chelate linked | Iron (III) diphenanthroline | Metal removal e.g. by chelation or precipitation |
| 12. Thermally Labile Linkers | Peroxides R—OO—R | Increase in temperature |
| 13. "Safety Catch" Labile Linkers | Methylthio- ethyl (Mte) Dithianes | Base; amines, others |

Additional examples of reversible crosslinkers are described in T. W. Green, *Protective Groups in Organic Synthesis*, John Wiley & Sons (Eds.) (1981). Any variety of strategies used for reversible protecting groups can be incorporated into a crosslinker suitable for producing crosslinked protein crystals capable of reversible, controlled solubilization. Various approaches are listed, in Waldmann's review of this subject, in *Angewante Chemie Inl. Ed. Engl.*, 35, p. 2056 (1996).

Other types of reversible crosslinkers are disulfide bond-containing crosslinkers. The trigger breaking crosslinks formed by such crosslinkers is the addition of reducing agent, such as cysteine, to the environment of the crosslinked protein crystals.

Disulfide crosslinkers are described in the *Pierce Catalog and Handbook* (1994–1995).

Examples of such crosslinkers include:
Homobifunctional (Symmetric)
DSS—Dithiobis(succinimidylpropionate), also know as Lomant's Reagent
DTSSP—3-3'-Dithiobis(sulfosuccinimidylpropionate), water soluble version of DSP
DTBP—Dimethyl 3,3'-dithiobispropionimidate•HCl
BASED—Bis-(β-[4-azidosalicylamido]ethyl)disulfide
DPDPB—1,4-Di-(3'-[2'-pyridyldithio]-propionamido) butane.
Heterobifunctional (Asymmetric)
SPDP—N-Succinimidyl-3-(2-pyridyldithio)propionate
LC-SPDP—Succinimidyl-6-(3-[2-pyridyldithio]propionate) hexanoate
Sulfo-LC-SPDP—Sulfosuccinimidyl-6-(3-[2-pyridyldlthio] propionate)hexanoate, water soluble version of LC-SPDP
APDP—N-(4-[p-azidosalicylamido]butyl)-3'-(2'-pyridyldithio)propionamide
SADP—N-Succinimidyl(4-azidophenyl)1,3'-dithiopropionate
Sulfo-SADP—Sulfosuccinimidyl(4-azidophenyl)1,3'-dithiopropionate, water soluble version of SADP
SAED—Sulfosuccinimidyl-2-(7-azido-4-methycoumarin-3-acetamide)ethyl-1,3'-dithiopropionate
SAND—Sulfosuccinimidyl-2-(m-azido-o-nitrobenzamido) ethyl-1,3'-dithiopropionate
SASD—Sulfosuccinimidyl-2-(p-azidosalicyamido)ethyl-1, 3'-dithiopropionate
SMPB—Succinimidyl-4-(p-maleimidophenyl)butyrate
Sulfo-SMPB—Sulfosuccinimidyl-4-(p-maleimidophenyl) butyrate
SMPT—4-Succinimidyloxycarbonyl-methyl-α-(2-pyridylthio)toluene
Sulfo-LC-SMPT—Sulfosuccinimidyl-6-(α-methyl-α-(2-pyridylthio)toluamido)hexanoate.

In order that this invention may be better understood, the following examples are set forth. These examples are for the purpose of illustration only and are not to be construed as limiting the scope of the invention in any manner.

EXAMPLES

Example 1

Preparation of Crosslinked Subtilisin Crystals
Crystallization of Subtilisin

One volume of Alcalase 2.5L (Novo Nordisk Bioindustrials, Franklinton, N.C.) was added to 2 volumes of a solution of 15% sodium sulfate (pH 5.5) prepared at 30–35° C. The crystallization solution was seeded with 1/2,000–1/500 volume seeds (30 mg/ml slurry of crystals in 15% sodium sulfate (pH 5.5), pH supported at 5.5 by adding NaOH. The seeded crystallization solution was incubated at 30–35° C., stirring by magnetic stirrer overnight. This yielded 60–80% (by activity) crystal rods, 10–50 μm, in length, 1–3 μm in width, after 24–48 hours.

Example 2

Crosslinking of Subtilisin Crystals

Subtilisin crystals were crosslinked using one of a variety of crosslinkers, including: glutaraldehyde, glyoxal, succinaldehyde, octanedialdehyde and epoxides.

Glutaraldehyde Crosslinking

Glutaraldehyde ("GA") (supplied as 50% in aqueous by Aldrich Chemical Co.) was diluted in deionized water at 4° C. in the various amounts listed in Table I below. For each ml of subtilisin crystals (27 mg/ml) in 15% sodium sulfate, 10 μl of the diluted glutaraldehyde was added to the slurry while shaking on a vortex at low speed (for amounts less than 5 ml) or stirring with an overhead stirrer at medium speed (for amounts 25 ml–500 ml). After mixing for the allotted crosslinking time, the samples were centrifuged for 20 seconds at maximum speed, the supernatant was discarded and replaced with 15% sodium sulfate. This "washing" was repeated a total of 5 times. The final resuspension was effected with 900 μl of 15% sodium sulfate.

TABLE I

Glutaraldehyde Crosslinking

| % GA-final | GA (ml) | H₂O (ml) | Crosslinking time (min) |
|---|---|---|---|
| 0.0076 | 1.0 | 64.96 | 60 |
| 0.0189 | 1.0 | 25.46 | 39 |
| 0.02 | 1.0 | 24.0 | 39, 81 |
| 0.05 | 1.0 | 9.00 | 15, 60, 89 |
| 0.08 | 1.0 | 5.25 | 39, 81 |
| 0.10 | 1.0 | 4.00 | 60, 81 |
| 0.125 | 1.0 | 3.00 | 3, 10, 17, 39 |
| 0.15 | 1.0 | 2.33 | 81, 120 |
| 0.20 | 1.0 | 1.50 | 19, 60, 120 |
| 0.231 | 1.0 | 1.16 | 10, 39, 120 |
| 0.3 | 1.0 | 0.67 | 60 |
| 0.5 | 1.0 | 0 | 60 |

Glyoxal Crosslinking

Glyoxal (supplied as 40% in aqueous by Aldrich Chemical Co.) ("GY") was added to the crystal suspension to give a final concentration of 0.01–1.0%. For each ml of subtilisin crystals (27 mg/ml) in 15% sodium sulfate 0.25 μl to 25 ml (0.01 to 1%) of the glyoxal was added to the slurry, while magnetically stirring at ambient temperature. After stirring for 1 hour, the crosslinked crystals were centrifuged and washed, as described for glutaraldehyde crosslinking.

Octanedialdehyde Crosslinking

Octanedialdehyde ("OA")(100% as supplied by DSM Chemie Linz), in the amounts shown in Table II below, was added undiluted to 1 ml of subtilisin crystal slurry (27 mg/ml in 15% sodium sulfate) while magnetically stirring at ambient temperature. Stirring was continued for the specified time of minutes or hours before the crosslinked crystals were centrifuged and washed, as described for glutaraldehyde crosslinking.

TABLE II

Octanedialdehyde Crosslinking

| % OA - final | OA (μl) | Crosslinking time |
|---|---|---|
| 0.05 | 0.5 | 16 h |
| 0.1 | 1.0 | 16 h |
| 0.2 | 2.0 | 16 h |
| 0.25 | 2.5 | 16 h |
| 0.5 | 5.0 | 16 h |
| 1.0 | 10.0 | 30 m, 1 h, 3 h, 16 h |

Succinaldehyde Crosslinking

Succinaldehyde ("SA")(40% as supplied by DSM Chemie Linz) was added undiluted, in the amounts shown in Table III below, to 1 ml of subtilisin crystal slurry (27 mg/ml in 15% sodium sulfate) while magnetically stirring at ambient temperature. Stirring was continued for the specified time of minutes or hours before the crosslinked crystals were centrifuged and washed, as described for glutaraldehyde crosslinking.

TABLE III

Succinaldehyde Crosslinking

| % SA - final | SA (μl) | Crosslinking time |
|---|---|---|
| 1.0 | 25 | 30 m, 1 h, 3 h |

Epichlorohydrin Crosslinking

A 10 μl aliquot of epichlorohydrin ("EP") (99%, Sigma Chemical Co., St. Louis, Mo.) was added undiluted to 1 ml of subtilisin crystal slurry (27 mg/ml in 15% sodium sulfate) while stirring at ambient temperature. Stirring was continued for the specified time of minutes or hours before the crosslinked crystals were centrifuged and washed, as described for glutaraldehyde crosslinking.

Epoxide Crosslinking

General Procedure

Crosslinking of subtilisin was carried out individually using one of a variety of epoxides. These included:
1) General name—DENACOL
   a) DENACOL EX-411
   b) DENACOL EX-421
   c) DENACOL EX-614
   d) DENACOL EX-201
   e) DENACOL EX-202; all obtained from Nagase American Corporation.
2) Obtained from Tokyo Kasei Inc. America:
   a) Neopentyl Glycol diglycidyl Ether (N448)("NP")
   b) Ethylene Glycol diglycidyl Ether (EO342)("EG").

The concentration of the epoxide was varied between 0.01 and 4.0% and the crosslinking time was varied from 1 hour to 72 hours. The procedure for addition to and removal of crosslinker from enzyme was as described above for glutaraldehyde crosslinking.

Subsequent crosslinking with glutaraldehyde (0.01 to 0.2%) for (1 hour to 5 hours) yielded strongly crosslinked enzyme crystals, insoluble in water, but active in the azocasein assay.

A sample of 1 ml of subtilisin crystal slurry (27 mg/ml in 15% sodium sulfate) was mixed by vortexing at low speed to assure a uniform suspension of crystals. Epoxide (10% solution in DMF) was added to the crystal slurry in the amounts specified in Table IV, and the mixture was shaken at ambient temperature. After the allotted time between 1 and 72 hours at ambient temperature, glutaraldehyde (10% in DMF) was added to the epoxide/crystal mixture and stirring was continued at ambient temperature for the time specified in Table IV. The resulting crosslinked enzyme crystals were washed 2× with 1% $(NH_4)_2SO_4$/10 mM $CaCl_2$ then 3× with water and finally 1× with 1% $(NH_4)_2SO_4$/10 mM $CaCl_2$ before resuspending in 1% $(NH_4)_2SO_4$/10 mM $CaCl_2$.

TABLE IV

Epoxide/Glutaraldehyde Crosslinking

| Epoxide Name | Epoxide Amount | Epoxide Crosslinking Time | Glutaraldehyde Amount | Glutaraldehyde Crosslinking Time |
|---|---|---|---|---|
| EX-411 | 0.01–4% | 1–72 h | 0.01–0.1% | 0.5–2 h |
| EX-421 | 0.01–4% | 1–72 h | 0.01–0.1% | 0.5–2 h |
| EX-614 | 0.01–4% | 1–72 h | 0.01–0.1% | 0.5–2 h |
| EX-201 | 0.01–4% | 1–72 h | 0.01–0.1% | 0.5–2 h |
| EX-202 | 0.01–4% | 1–72 h | 0.01–0.1% | 0.5–2 h |
| NP (N448) | 0.01–4% | 1–72 h | 0.01–0.1% | 0.5–2 h |
| EG (EO342) | 0.01–4% | 1–72 h | 0.01–0.1% | 0.5–2 h |

Large Scale Preparation of A Preferred Epoxide Sample

Prior to crosslinking, a sample of 380 ml of crystalline subtilisin in 15% sodium sulfate (27 mg/ml) was mixed by overhead stirring at ambient temperature for 5 minutes to assure a uniform suspension of crystals. Neopentyl glycol diglycidyl ether (3.838 ml of a 10% solution in DMF) was added to the crystal slurry and the mixture was stirred at ambient temperature. After 5 hours at ambient temperature, 3.838 ml of glutaraldehyde (10% in DMF) was added to the epoxide/crystal mixture and stirring was continued at ambient temperature for 1.5 hours. The resulting crosslinked enzyme crystals were washed 2× with 1% $(NH_4)_2SO_4$/10 mM $CaCl_2$ then 3× with water and finally 1× with 1% $(NH_4)_2SO_4$/10 mM $CaCl_2$, before resuspending in 1% $(NH_4)_2SO_4$/10 mM $CaCl_2$.

Example 3

Activity Assay

In order to test the activity of crosslinked protein crystals according to this invention, as well as other enzyme samples, we developed the following azocasein assay.

Materials:
2.0M Tris Buffer. 500 ppm $CaCl_2$
0.2M Tris Buffer. 50 ppm $CaCl_2$
50% urea
Azocasein
5% trichloroacetic acid ("TCA")
Alcalase (2.5L)
ChiroCLEC-BL™ (crosslinked subtilisin crystals, available from Altus Biologics, Inc., Cambridge, Mass.)

The assay was carried out, preparing azocasein just prior to use, by dissolving 600 mg azocasein with 10 ml of 50% urea and vortexing lightly to complete the dissolution. Then 10 ml 2.0M Tris was added and vortexed to mix, increasing the volume to 100 ml by adding deionized water.

The stock solutions of the enzyme to be assayed in 0.2M Tris were prepared, to provide 50 µl aliquots to be assayed, as follows:
Without detergent: 0.03 mg/ml Alcalase (soluble, uncrosslinked subtilisin Carlsberg 80.3 mg/ml) 3.0 mg/ml ChiroCLEC-BL™.

With 120 µl detergent/ml solution: 0.03 mg/ml Alcalase 3.0 mg/ml ChiroCLEC-BL™.

We added 50 µl aliquots of enzyme to 150 µl of 0.2M Tris and placed the mixtures in 5 ml test tubes with micro-stir bars. We then warmed both the test tubes and the azocasein at 40° C. for 1 minute using a metal heating block. After that, we added 1 ml of the azocasein to each tube and stirred at 40° C. for 15 minutes using the heating block at stir speed 4. We then added 2 ml TCA to each tube, mixing by vortex, and placed the tubes in an ice bath immediately, allowing the samples to stand at 0° C. for 20 minutes. We microfuged the samples for 5 minutes at maximum rpm and microfiltered, if necessary. We measured absorbance of the expressed activity in abs·units/mg protein·min supernatant at $\lambda$390. In this assay, all measurements were done in triplicate. Controls were void of enzyme but contained detergent if it was present in the assay. This time=0 assay was repeated at time=15 minutes and other times, if necessary.

The detergents used in the various assays included Tide, Wisk and Ciba-Geigy detergents #15, #16 and #44 ("Ciba detergents"). Ciba detergent #15 constitutes a typical European detergent formulation—liquid (aqueous) detergent on the basis of 15% alkylbenzene sulfonate, 14% fatty alcohol ethoxylate and 10% fatty acid salt (soap). Ciba detergent #16 constitutes a typical United States detergent formulation—liquid (aqueous) detergent on the basis of 7.5% alkyl benzene sulfonate, 10% fatty alcohol ethoxylate and 17% alkyl either sulfate. Ciba detergent #44 constitutes a typical compact detergent formulation—liquid (aqueous) detergent on the basis of 6% fatty alcohol ethoxylate, 23% alkyl ether sulfate and 10% sodium citrate. Ciba detergents #15, #16 and #44 may be obtained upon request from Ciba Specialty Chemicals Corp., Division Consumer Care Chemicals, Greensboro, N.C.

We prepared assay stock solutions from dilution stocks, and carried out the assays, as follows.
Activity Assay—200× Dilution—Crosslinked Subtilisin Crystals and Crystalline Subtilisin in Heavy Duty Liquid Detergent (Ciba #15, Ciba #44, Tide and Wisk)

Stocks A, B, C and D were prepared in 10 ml neoprene tubes as follows.
Stock A: Crosslinked Subtilisin Crystals Prepared According to this Invention (~27 mg/ml)

We centrifuged 37 µl slurry of crosslinked subtilisin crystals (equal to 1 mg crosslinked enzyme crystals) to remove supernatant, added 1 ml detergent and vortexed to mix. A 50 µl aliquot of the resulting mixture was added to 9.95 ml water, to a final concentration of 5 µg/ml.
Stock B: Uncrosslinked Subtilisin Crystals (~27 mµ/ml)

We centrifuged 37 µl slurry of subtilisin crystals (equal to 1 mg enzyme crystals) to remove supernatant, added 1 ml detergent and vortexed to mix. A 50 µl aliquot of the resulting mixture was added to 9.95 ml water, to a final concentration of 5 µg/ml.
Stock C: Alcalase We added 18.75 µl Alcalase (80.3 mg/ml) to 3 ml detergent and vortexed to mix. A 50 µl aliquot of the resulting mixture was added to 9.95 ml water, to a final concentration of 2.5 µg/ml.
Stock D: Detergent A 50 µl aliquot of detergent was added to 9.95 ml water.
Azocasein stock (6 mg/ml) was prepared as described above. Upon dilution of Stock A and B to 5 µg/ml, the t=0 assay was set up immediately and carried out as described above, except that the amount of stock sample used was 200 µl, instead of 50 µl+150 µl 0.2M Tris. While the tubes were heating for 1 minute at 40° C., two additional samples of 2 ml each of Stocks A, B and C were placed in 1.5 ml microcentrifuge tubes and heated to 52° C. while shaking for further testing after 5 minutes and 15 minutes dilution with heating.

Activity Assay—670× Dilution—Crosslinked Subtilisin Crystals and Crystalline Subtilisin in Detergent Concentrate (Ciba #16)

Stocks A, B, C and D were prepared in 10 ml neoprene tubes as follows.

Stock A: Crosslinked Subtilisin Crystals Prepared According to this Invention (~27 mg/ml)

We centrifuged 124 µl slurry of crosslinked subtilisin crystals (equal to 3.35 mg crosslinked enzyme crystals) to remove supernatant, added 1 ml detergent and vortexed to mix. A 50 µl aliquot of the resulting mixture was added to 33.45 ml water, to a final concentration of 5 µg/ml.

Stock B: Uncrosslinked Subtilisin Crystals (~27 mg/ml)

We centrifuged 124 µl slurry of subtilisin crystals (equal to 3.35 mg enzyme crystals) to remove supernatant, added 1 ml detergent and vortexed to mix. A 50 µl aliquot of the resulting mixture was added to 33.45 ml water, to a final concentration of 5 µg/ml.

Stock C: Alcalase

We added 167 µl Alcalase (80.3 mg/ml) to 8 ml detergent and vortexed to mix. A 50 µl aliquot of the resulting mixture was added to 33.45 ml water, to a final concentration of 2.5 µg/ml.

Stock D: Detergent

A 50 µl aliquot of detergent was added to 33.45 ml water.

Azocasein stock (6 mg/ml) was prepared as described above. The t=0 assay was set up immediately and carried out as described above, except that the amount of stock sample used was 200 µl, instead of 50 µl, plus 150 µl 0.2M Tris buffer. While the tubes were heating for 1 minute at 40° C., two additional samples of 2 ml each of Stocks A, B and C were placed in Eppendorf tubes and heated to 40° C. while shaking for further testing after 5 minutes and 15 minutes dilution with heating.

Example 4

Stability Study

In order to test the stability of crosslinked enzyme crystals according to this invention, as well as other enzyme samples, we developed the following assays.

Azocasein Assay—Stability Study 52° C.

First, we prepared stock solutions of the enzyme samples in detergent in 2 ml Eppendorf tubes with screw caps. After incubating the mixtures in a water bath at 52° C. for the appropriate times, we added 1.47 ml of 0.2M Tris buffer to one of each enzyme sample tube, and mixed well. To assay for activity after the appropriate time of incubation followed by dilution, we removed a 50 µl aliquot from each tube and assayed as described below. The remaining samples of enzyme/detergent stocks were placed in a water bath at 52° C., with further aliquots being removed for assay at specific times.

The assay was performed by adding 50 µl enzyme sample to 150 µl 0.2M Tris buffer and heating to 40° C. for 1 minute. At a constant 40° C. temperature, we then added 1.0 ml azocasein stock (as described in Example 1) to each sample, stirring for 15 minutes using a heating block at stir speed 4. We then added 2 ml TCA to each tube, mixing by vortex, and placed the tubes in an ice bath immediately, allowing the samples to stand at 0° C. for 20 minutes. We microfuged the samples for 5 minutes at maximum rpm and microfiltered, if necessary. We measured absorbance of the supernatant at $\lambda 390$ and expressed activity as abs·units/mg protein·min. In this assay, all measurements were done in triplicate. Controls were void of enzyme but contained detergent if it was present in the assay.

In order to assess activity as part of stability studies carried out at 52° C., we prepared assay stock solutions from dilution stocks, and carried out the assays, as follows.

For Alcalase Stocks:

Stock A:

Alcalase (80.3 mg/ml) in commercial detergent (Tide or Wisk, deactivated by heating at 70° C. for 4 hours)—final concentration=0.25 mg/ml. The stock was prepared by adding 31.2 µl Alcalase to 9.97 ml detergent. A 200 µl aliquot of the resulting mixture was placed in each of several 2 ml Eppendorf tubes (3× for t=0, 30 and others).

Stock B:

Alcalase (80.3 mg/ml) in Ciba detergent (Ciba #15, Ciba #16 or Ciba #44)—final concentration=0.25 mg/ml. The stock was prepared by adding 31.2 µl Alcalase to 9.97 ml detergent. A 200 µl aliquot of the resulting mixture was placed in each of several 2 ml Eppendorf tubes (3× for t=0, 1 hour and 4–6 hours).

Stock C:

Commercial detergent (Tide or Wisk, deactivated by heating at 70° C. for 4 hours) 3× (200 µl of the above in 2 ml Eppendorf tubes).

Stock D:

Ciba detergent (Ciba #15, Ciba #16 or Ciba #44) 3× (200 µl of the above in 2 ml Eppendorf tubes).

The t=0 assay was performed immediately after 1.47 ml of 0.2 M Tris was added to one of each of tubes containing Stocks A–D and the contents mixed well. Remaining samples of Stocks A–D were placed in a water bath and heated to 52° C. Otherwise, the assays were carried out as described above.

For Crosslinked Subtilisin Crystals and Crystalline Subtilisin

Stocks A, B, C and D were prepared in 2 ml Eppendorf tubes with screw caps as follows.

Stock A:

ChiroCLEC-BL™ in commercial detergent (denatured Tide or Wisk)—final concentration=25 mg/ml. The stock was prepared by centrifuging 3.12 ml enzyme slurry to remove water and then diluting the enzyme to 10 ml with detergent. A 200 µl aliquot of the resulting mixture was placed in each of several 2 ml Eppendorf tubes (4× for t=0, 24 hours, 48 hours and 72 hours).

Stock B:

ChiroCLEC-BL™ in Ciba detergent (Ciba #15, Ciba #16 or Ciba #44)—final concentration=25 mg/ml. The stock was prepared by centrifuging 3.12 ml enzyme slurry to remove water and then diluting the enzyme to 10 ml with detergent. A 200 µl aliquot of the resulting mixture was placed in each of several 2 ml Eppendorf tubes (4× for t=0, 24 hours, 48 hours and 72 hours at 52° C.).

Stock C:

Commercial detergent (Tide or Wisk, deactivated by heating at 70° C. for 4 hours) 4× (200 µl of the above in 2 ml Eppendorf tubes).

Stock D:

Ciba-Geigy detergent (Ciba #15, #16 or #44, depending on which detergent was chosen for Stock B) 4× (200 µl of the above in 2 ml Eppendorf tubes).

The t=0 assay was set up immediately after 1.47 ml of 0.2M Tris was added to one of each of tubes containing Stocks A–D and the contents mixed well. Remaining samples of Stocks A–D were placed in a water bath and heated to 52° C. Otherwise, the assays were carried out as described above.

For Crosslinked Subtilisin Crystals and Crystalline Subtilisin

Stocks A, B and C were prepared in 2 ml Eppendorf tubes with screw caps as follows.

Stock A:

Uncrosslinked subtilisin crystals (~27 mg/ml) in Ciba detergent (Ciba #15, #16 or #44)—final concentration=~1 mg/ml. The stock was prepared by centrifuging 50 μl crystal slurry to remove supernatant, then adding 1.35 ml detergent (Ciba #15, Ciba #16 or Ciba #44) to a final concentration of 1 mg/ml. An 80 μl aliquot of the resulting mixture was placed in each of several 2.0 ml Eppendorf tubes (3× for t=0, 15 minutes and others).

Stock B:

Crosslinked subtilisin crystals according to this invention (~27 mg/ml) in Ciba detergent (Ciba #15, #16 or #44)—final concentration=~1 mg/ml. The stock was prepared by centrifuging 50 μl crystal slurry to remove supernatant, then adding 1.35 ml detergent, to a final concentration of 1 mg/ml. An 80 μl aliquot of the resulting mixture was placed in each of several 2.0 ml Eppendorf tubes (3× for t=0, 15 minutes and others).

Stock C:

Ciba detergent (Ciba #15, #16 or #44)—3× (80 μl of the above in 2.0 ml tubes).

The t=0 assay was set up immediately after 1.8 ml of water was added to one of each of tubes containing Stocks A–C and the contents mixed well. Remaining samples of Stocks A–C were placed in a water bath and heated to 52° C. Otherwise, the assays were carried out as described above, except for the addition of 150 μl 0.2 M Tris buffer instead of 200 μl.

Azocasein Assay—Stability Study 40° C.

First, we prepared stock solutions of the enzyme samples in detergent in 2 ml Eppendorf tubes with screw caps. To assay stability at t=0, we added 1.8 ml of deionized water to a 25 μl of each sample and mixed well. We removed a 25 μl aliquot from each tube and assayed as described below. The remaining samples of enzyme/detergent stocks were placed in a water bath at 40° C., with further aliquots being removed for assay at specific times.

The assay was performed by adding 25 μl of the diluted enzyme sample to 175 μl 0.2M Tris buffer and heating to 40° C. for 1 minute. At a constant 40° C. temperature, we then added 1.0 ml azocasein stock (as described in Example 3) to each sample, stirring for 15 minutes using a heating block at stir speed 4. We then added 2 ml TCA to each tube, mixing by vortex, and placed the tubes in an ice bath immediately, allowing the samples to stand at 0° C. for 20 minutes. We microfuged the samples for 5 minutes at maximum rpm and microfiltered, if necessary. We measured absorbance of the supernatant at λ390 and expressed activity as abs·units/mg protein·min. In this assay, all measurements were done in triplicate. Controls were void of enzyme but contained detergent if it was present in the assay.

In order to assess activity as part of stability studies carried out at 40° C., we prepared assay stock solutions from dilution stocks, and carried out the assays, as follows.

Stock A: Crosslinked Subtilisin Crystals According to this Invention (~27 mg/ml)

We centrifuged 124 μl slurry of crosslinked subtilisin crystals (equal to 3.35 mg crosslinked enzyme crystals) to remove supernatant, added 1 ml detergent and vortexed to mix, to a final concentration of 3.35 mg/ml.

Stock B: Uncrosslinked Subtilisin Crystals (~27 mg/ml)

We centrifuged 124 μl slurry of subtilisin crystals (equal to 3.35 mg enzyme crystals) to remove supernatant, added 1 ml detergent and vortexed to mix, to a final concentration of 3.35 mg/ml.

Stock C: Alcalase

We added 20.9 μl Alcalase (80.3 mg/ml) to 1 ml Ciba detergent (Ciba #15, Ciba #16 or Ciba #44) and commercial detergent (Tide or Wisk, denatured by heating at 70° C. for 4 hours) and vortexed to mix, to a final concentration of 1.67 mg/ml.

Stock D: Detergent

One ml of commercial detergent (Tide or Wisk, deactivated by heating at 70° C. for 4 hours) and Ciba detergents #15, #16 and #44. A 25 μl aliquot of each stock was added to 1.8 ml of deionized water and mixed well. A further 25 μl aliquot of the diluted stock was added to each reaction tube.

The t=0 assay was performed immediately after 175 μl of 0.2M Tris was added to each tube containing 25 μl of the various stock samples. Remaining samples of Stocks A–D were placed in a water bath and heated to 40° C. Otherwise, the assays were carried out as described above.

Example 5

Dissolution Studies

We also assessed the characteristics of crosslinked enzyme crystals according to this invention, as well as other enzyme samples, with respect to dissolution in concentrate and upon dilution, as detailed below. Stock solutions were prepared and diluted as described above. The resulting dispersions were heated at 40° C. and analyzed under a microscope at 250× for dissolution progress.

Example 6

Results of Activity and Stability Assays

Crosslinked enzyme crystals of subtilisin, as described above, as well as soluble enzymes and other commercial enzymes, alone and in the presence of commercial detergents, were tested for activity in the azocasein assay, as described above. Catalyst concentrations for equivalent activities were determined for Alcalase, ChiroCLEC-BL™, Wisk with active protease and Tide with active protease:

ChiroCLEC-BL™: 150 μg/6 μl detergent 0.4–0.5 absorbance units

Alcalase: 15 μg/6 μl detergent 0.5–0.6 absorbance units

Tide: 6 μl detergent approximately 0.6 absorbance units

Wisk: 6 μl detergent approximately 0.6 absorbance units.

The dilution studies (discussed supra) were started by assessing the activities of Alcalase and uncrosslinked crystals of Alcalase in Ciba detergents #15 and #16. Initial activities were comparable and losses of up to ~50% were seen after 15 minutes at 52° C.

Table V summarizes the stability of samples of Alcalase (0.25 mg/ml) and ChiroCLEC-BL™ (25 mg/ml) in denatured Wisk or Tide detergent, or in Ciba detergents #15 and #16 at 52° C. Activity was measured by the azocasein assay.

TABLE V

Stability of Subtilisin in Detergents at 52° C.

| Detergent | Alcalase $T_{1/2}$ at 52° C. | ChiroCLEC-BL ™ $T_{1/2}$ at 52° C. |
|---|---|---|
| #15 | less than 15 min | >>100 hours |
| #16 | less than 15 min | >>100 hours |
| Tide (denatured) | 16 hours | >>100 hours |
| Wisk (denatured) | 60–70 hours | >>100 hours |

We also assessed the stability of various enzymes in Ciba detergent #15 at 52° C. The results are depicted in Table VI below:

TABLE VI

Stability of Subtilisin in Ciba Detergent #15 at 52° C.

| Catalyst | Initial Activity | Activity 15 min dilute at 52° C. | $T_{1/2}$ in concentrate at 52° C. |
|---|---|---|---|
| Alcalase | 36 | 14 | ~15 min |
| Alcalase | 33 | 13 | ~15 min |
| OA 0.1%, 16 h | 34 | 18 | ~15 min |
| OA 1%, 1 h | 23 | 17 | ~30 min |
| OA 1%, 3 h | 10 | 14 | ~30 min |
| GA 0.05%, 30 min | 27 | 16 | ~40 min |
| GA 0.05%, 10 min | 35 | 15 | ~40 min |

All of the crosslinked crystals prepared as described in the table above which had half-lives in detergent concentrate of ~30 minutes or more also had good solubility profiles.

In addition, we assessed the stability of various enzymes in Ciba detergent #15 versus Ciba detergent #16 at 40° C. The results are depicted in the Table VII below:

TABLE VII

Stability of Subtilisin in Ciba Detergent #15 vs. #16 at 40° C.

| Catalyst | Initial Activity | $T_{1/2}$ in #15 concentrate at 40° C. | $T_{1/2}$ in #16 concentrate at 40° C. |
|---|---|---|---|
| Alcalase | 33 | 10 h | 2.5 h |
| GA 0.05%, 30 min | 27 | 7 h | ~10 h |
| OA 0.1%, 16 h | 32 | 9 h | 8 h |
| OA 0.2%, 16 h | 15 | 12 h | 16 h |

We also assessed the effects of crosslinking time on activity and stability of the resulting crosslinked enzyme crystals. These results are summarized in the tables below. In Table VIII, an asterisk indicates values measured by incubating 25 μl in a 2 ml tube and "Xs" denotes uncrosslinked protein crystals.

In preparing the crosslinked protein crystals described in Tables VIII, IX and X, the protein crystals were crystallized as described in Example 1 and crosslinked with glutaraldehyde as described in Example 2, using the crosslinking times and glutaraldehyde concentrations set forth in that example, or those specified in the tables.

TABLE VIII

Crosslinking Time vs. Concentration of Glutaraldehyde on Stability of Subtilisin in Ciba Detergent #16 at 40° C.

| GA (%) | Cross-linking Time | Activity abs/mg/min t = 0 | Activity abs/mg/min t = 18 h | Stability, 18 h % of Xs, t = 0 |
|---|---|---|---|---|
| (Xs) 0 | 0 | 33.6 | 1.1 | 3.3 |
| (Xs) 0 | 0 | 31.7 | 2.6* | 8.2* |
| 0.0189 | 10.0 | 28.5 | 5.2 | 16.5 |
| 0.0189 | 10.0 | 31.3 | 5.7 | 17.8 |
| 0.0189 | 39.3 | 14.1 | 5.4 | 17.0 |
| 0.0189 | 39.3 | 14.3 | 5.0 | 15.8 |
| 0.05 | 5.0 | 20.7 | 3.8 | 12.0 |
| 0.05 | 15.0 | 16.4 | 7.0 | 22.1 |
| 0.05 | 18.6 | 19.6 | 8.7 | 27.4 |
| 0.05 | 18.6 | 17.8 | 9.8 | 30.9 |
| 0.05 | 60.0 | 0 | 13.5 | 42.6 |
| 0.05 | 60.0 | 3.0 | 14.7 | 46.4 |
| 0.125 | 3.0 | 18.3 | 9.1 | 28.7 |
| 0.125 | 3.0 | 15.4 | 9.0 | 28.4 |
| 0.125 | 10.0 | 7.9 | 14.9 | 46.9 |
| 0.125 | 10.0 | 9.5 | 14.8 | 46.6 |
| 0.125 | 10.0 | 7.9 | 14.7 | 46.4 |
| 0.125 | 10.0 | 9.5 | 13.4 | 42.1 |
| 0.125 | 10.0 | 9.4 | 12.2 | 38.5 |
| 0.125 | 10.0 | 8.1 | 12.2 | 38.5 |
| 0.125 | 10.0 | 8.3 | 16.0 | 50.5 |
| 0.125 | 17.0 | 5.4 | 14.0 | 44.2 |
| 0.125 | 17.0 | 6.4 | 15.3 | 48.3 |
| 0.125 | 39.3 | 2.1 | 3.3 | 10.4 |
| 0.125 | 39.3 | 1.0 | 5.8 | 18.3 |
| 0.125 | 39.3 | 1.1 | 4.4 | 13.9 |
| 0.125 | 39.3 | 1.7 | 4.5 | 14.3 |
| 0.125 | 39.3 | 1.6 | 5.7 | 18.0 |
| 0.125 | 39.3 | 0.9 | 3.3 | 10.4 |
| 0.125 | 68.6 | 1.3 | 3.1 | 9.9 |
| 0.2 | 5.0 | 10.4 | 12.1 | 38.2 |
| 0.2 | 15.0 | 2.5 | 9.0 | 28.4 |
| 0.2 | 18.6 | 1.8 | 6.9 | 21.8 |
| 0.2 | 18.6 | 0.8 | 3.1 | 9.8 |
| 0.2 | 60.0 | 0.4 | 1.3 | 4.1 |
| 0.2 | 60.0 | 1.4 | 1.4 | 4.4 |
| 0.231 | 10.0 | 2.7 | 13.0 | 41.0 |
| 0.231 | 10.0 | 4.8 | 11.7 | 37.0 |
| 0.231 | 39.3 | 0.5 | 1.1 | 3.5 |
| Alcalase | | 28.0 | 3.1* | 9.8* |
| Alcalase | | 32.9 | 0.2 | 1.0 |

In Table IX, an asterisk indicates that crystals were crushed during crosslinking and dash marks indicate that no measurements were taken at those points. All samples were prepared at 1 ml (27 mg) scale.

TABLE IX

Activity of Glutaraldehyde Crosslinked Subtilisin in Ciba Detergent #16 at 40° C.

| GA (%) | Crosslinking time (min) | Activity at 40° C. (abs/mg/min) | | | | | | |
|---|---|---|---|---|---|---|---|---|
| | | t = 0 | 18 h | 39 h | 63 h | 90 h | 90 h | 6 days |
| (Xs) 0 | 0 | 33.6 | 1.1 | — | — | — | — | — |
| 0.0076 | 60 | 14.1 | 3.0 | — | — | — | — | — |
| 0.02 | 39 | 12.0 | 7.7 | — | — | — | — | — |
| 0.02 | 80 | 6.9 | 11.5 | — | — | — | 0 | — |
| 0.02* | 80 | 12.2 | 26.2 | 10.7 | 3 | — | — | — |
| 0.05* | 31 | 13.5 | 26.3 | 9.8 | 5.3 | — | — | — |
| 0.05 | 60 | 4.9 | 17.7 | 7.9 | 2.4 | — | — | 1.0 |
| 0.05* | 60 | 8.7 | 27.3 | 12.5 | 7.3 | — | — | — |
| 0.05 | 89 | 1.3 | 12.1 | — | — | — | 3.7 | — |
| 0.08 | 39 | 2.2 | 12.6 | — | — | — | 5.3 | — |

TABLE IX-continued

Activity of Glutaraldehyde Crosslinked Subtilisin in Ciba Detergent #16 at 40° C.

| GA (%) | Crosslinking time (min) | t = 0 | 18 h | 39 h | 63 h | 90 h | 90 h | 6 days |
|---|---|---|---|---|---|---|---|---|
| 0.08 | 81 | 0.8 | 3.9 | — | — | 5.8 | — | 3.9 |
| 0.08* | 81 | 9.8 | — | — | — | 10.2 | — | — |
| 0.125 | 3 | 16.4 | 9.7 | 1.7 | 0.3 | — | — | — |
| 0.125 | 10 | 9.4 | 14.8 | 9.4 | 1.9 | — | — | — |
| 0.125 | 17 | 6.4 | 15.3 | 11.5 | 8.5 | 4.6 | — | — |
| 0.2 | 5 | 10.4 | 12.7 | 5.1 | 0.3 | — | — | — |
| 0.23 | 10 | 4.8 | 11.7 | 10.0 | 8.5 | 5.2 | — | — |
| Alcalase | | | 30.5 | 1.6 | | | | |

Activity at 40° C. (abs/mg/min)

TABLE X

Conditions for Larger Scale Crosslinked Enzyme Crystal Preparation - Stability of Glutaraldehyde Crosslinked Subtilisin in Ciba Detergent #16 at 40° C.

| GA (%) | Crosslinking time (min) | t = 0 | 18 h | | | |
|---|---|---|---|---|---|---|
| (Xs) | 0 | 33.9 | — | | | |

| | | t = 0 | 16 h | 38 h | 59 h | 110 h |
|---|---|---|---|---|---|---|
| *0.05 | 60 | 23.2 | 16.8 | 5.9 | 1.9 | 5.6 |
| *0.08 | 80 | 14.4 | 12.2 | 4.1 | 2.4 | — |
| *0.1 | 80 | 8.0 | 13.6 | 5.5 | 3.1 | 1.4 |
| *0.125 | 60 | 9.3 | 20.9 | 13.6 | — | 2.3 |
| *0.15 | 80 | 3.8 | 11.2 | 7.4 | 5.2 | 2.8 |
| *0.231 | 60 | 5.2 | 9.9 | 9.3 | 6.6 | 8.3 |
| *1.0 | 60 | 1.3 | 2.5 | 2.2 | 1.1 | 2.4 |

| | | t = 0 | 24 h | 48 h | 72 h | 120 h | 168 h | 264 h |
|---|---|---|---|---|---|---|---|---|
| §0.25 | 120 | 4.8 | 9.5 | 7.7 | 6.7 | 5.7 | 4.3 | 4.4 |
| §0.20 | 120 | 2.6 | 9.5 | 8.6 | 8.7 | 5.6 | — | 4.5 |
| §0.15 | 120 | 5.2 | 14.3 | 9.6 | 5.6 | 3.7 | — | 1.2 |
| §0.1-NP/ §0.1 GA | 5 h/1.5 h | 9.6 | 10.2 | 6.3 | — | — | 5.7 | |

Stability at 40° C. (abs/mg/min)

In Table X, an asterisk indicates that crosslinkings were carried out at a 1–2 g scale, § indicates that crosslinkings were carried out at a 10 g scale on previously crushed crystals and dash marks indicate that no measurements were taken at those points.

FIG. 1 graphically depicts the stability of 10 g scale preparations of crosslinked subtilisin crystals according to this invention in Ciba detergent #16 at 40° C. In FIG. 1, "Altus I" represents crystals crosslinked with 0.25% glutaraldehyde for 2 hours; "Altus II" represents crystals crosslinked with 0.20% glutaraldehyde for 2 hours; "Altus III" represents crystals crosslinked with 0.15% glutaraldehyde for 2 hours and "Altus IV" represents crystals crosslinked with 0.1% neopentyl glycol diglycidyl ether for 5 hours, followed by 0.1% glutaraldehyde for 1.5 hours. All the crosslinked samples were crushed prior to crosslinking using a Brinkman Polytron Homogenizer, then prepared on a 10 g scale and monitored by the azocasein assay over one week at 40° C.

Example 7

Results of Dissolution Study

The dissolution study demonstrated whether various crosslinked enzyme crystals dissolve in concentrate and the extent to which they dissolve upon dilution under conditions of use, for example under wash conditions. Representative results of this test are included in the tables below, in which "+" indicates that the sample dissolved, "−" indicates that the sample did not dissolve, "−/+" indicates that the sample dissolved somewhat (1 mg/ml in detergent liquid). In the tables, "GP" denotes crystals crosslinked as described infra for GA crosslinking using, instead, ultrapure glutaraldehyde (supplied as an 8% aqueous solution by the Sigma Chemical Co.) which was not diluted prior to addition to the protein crystals.

TABLE XI

Detergent Liquid Incubation Study - Dissolution Study - Concentrate 14 h at 40° C.

| Catalyst | Ciba #15 | Ciba #16 | Ciba #44 | Tide |
|---|---|---|---|---|
| OA 1%, 16 h | − | −/+ | + | − |
| OA 0.5%, 16 h | − | − | + | − |
| OA 0.1%, 16 h | − | + | + | − |
| OA 0.2%, 16 h | − | −/+ | + | − |
| GA 0.5%, 1 h | − | −/+ | + | − |
| GA 0.9%, 1 h | − | − | − | − |
| GA 0.7%, 1 h | − | − | + | − |
| EP 1.0%, 20 min | −/+ | + | + | − |
| GP 0.08%, 20 min | − | −/+ | + | − |
| CLECBL ™ | − | − | − | − |
| Crystals (uncross-linked) | + | + | + | − |

TABLE XII

Detergent Liquid Incubation Study - Dissolution Study - 200 fold Dilution 20 minutes at 52° C.

| Catalyst | Ciba #15 | Ciba #16 | Ciba #44 | Tide |
|---|---|---|---|---|
| OA 1%, 16 h | −/+ | −/+ | + | − |
| OA 0.5%, 16 h | − | + | + | − |
| OA 0.1%, 16 h | − | + | + | + |
| OA 0.2%, 16 h | −/+ | + | + | − |
| GA 0.5%, 1 h | − | −/+ | + | − |
| GA 0.9%, 1 h | − | + | + | − |
| GA 0.7%, 1 h | − | − | + | − |
| EP 1.0%, 20 min | + | + | + | + |
| GP 0.08%, 20 min | − | + | + | − |
| CLECBL ™ | − | − | − | − |
| Crystals (uncross-linked) | + | + | + | + |

As demonstrated in the tables above, crosslinked enzyme crystals according to this invention are essentially insoluble in concentrated detergent and essentially soluble in diluted detergent under wash conditions.

Example 8

Summary of Properties of Crosslinked Enzyme Crystals of This Invention

Table XIII below summarizes the overall stability/instability, activity and dissolution properties in Ciba detergent #15 of crosslinked subtilisin crystals prepared according to this invention using dialdehydes.

TABLE XIII

| Cross-linker | Solubility in Ciba #15 | Solubility on Dilution | Activity (t = 0) | Stability at 52° C. |
|---|---|---|---|---|
| Glyoxal | low | dissolve at 52° C. | high | low |
| Succini-maldehyde | low | dissolve at 52° C.; partially dissolve at 25° C. | 17–66% of Alcalase | ND |
| Glutaral-dehyde | very low | dissolve at 52° C.; partially to fully dissolve at 25° C. | 1–100% of Alcalase | low 52° C. moderate 40° C. |
| Octane-dialdehyde | very low % | dissolve at 52° C.; partially to fully dissolve at 25° C. | 30–66% of Alcalase | low 52° C. moderate 40° C. |

As demonstrated in Table XIII above, the crosslinked enzyme crystals of the present invention are insoluble and, therefore, stable under storage conditions, while quickly releasing their activity under conditions of use. Advantageously, the crosslinked enzyme crystals of this invention exhibit activity similar to their soluble or uncrosslinked crystallized counterparts under conditions of use, while displaying 5–6 fold improved stability, as well as favorable dissolution properties.

Example 9

Effect of Change of Chemical Composition On Crosslinked Subtilisin Crystals

We crystallized subtilisin as described in Example 1 and crosslinked the resulting crystals as described in Example 2, using GA 1%/1 hour. When 100 μL (2.2 mg) of the resulting crosslinked subtilisin crystals was suspended in 1.5 mL of 33.3% of acetonitrile/phosphate buffer (0.3 M, pH 7.5), the crystals were completely dissolved after 45 minutes at 40° C.

Using similar conditions, suspending the crosslinked subtilisin crystals in 1.2 mL of 16.7% acetonitrile/buffer, the crystals were completely dissolved after 5 hours.

| | Activity (U) | | |
|---|---|---|---|
| time | in 100% buffer | ACN/16.7% Buffer | ACN/33.3% Buffer |
| 0 | 27.3 | 27.3 | 27.3 |
| 1.5 h | 27.3 | — | 7.4* |
| 3.3 h | 27.3 | 25.5 | |
| 7.0 h | 27.3 | 24.0** | |

-continued

| | Activity (U) | | |
|---|---|---|---|
| time | in 100% buffer | ACN/16.7% Buffer | ACN/33.3% Buffer |

*crystals were completely dissolved at this time.
**crystals were not completely dissolved.

Assay: 0.2 mmol (75.8 mg) of TAME in 2.5 mL phosphate buffer was incubated with each crosslinked subtilisin crystal sample (equal to 0.044 mg enzyme crystals) suspension (or solution) at room temperature. One unit hydrolyzed 1.0 μmole of TAME per min. per mg crosslinked crystals.

The results above illustrate the trigger of addition of organic solvent to the environment of crosslinked protein crystals of this invention.

Example 10

Wash Performance of Detergents Containing Crosslinked Subtilisin Crystals

We assessed the activity and storage stability of crosslinked enzyme crystals of this invention in liquid detergent, using a washing assay designed to test the ability of the detergent to remove stains from a fabric.

Washing Assay

Preparation of Fabric

Cloth samples of the same size and weight were cut from the same bolt:

5 g of soiled test cloth and 5 g of cotton ballast with no soil (Ciba No. 1-3005).

Prior to washing the samples, we measured the light intensity (=lightness) remitted by the soiled fabric samples (as described below).

Preparation of Detergent Solution

The sample of liquid detergent to be tested was heated in a flask for two hours at 20° C. The sample was then homogenized by vigorous shaking and 0.8 g of the detergent was removed from the flask and added to 200 ml of tap water (20° C.) in a metallic beaker. The aqueous detergent solution was stirred for 60 seconds.

Washing

A sample of soiled test cloth and a sample of unsoiled ballast were placed together into the beaker containing the aqueous detergent solution. The beaker was closed tightly and immediately inserted into a pre-heated (40° C.) washing machine (Unitest, manufactured by Hereus, Switzerland). During the washing process, the beaker was rotated constantly in a water bath heated to 40° C. As a result, the contents of the beaker continuously warmed, up to a temperature of 40° C.

Exactly 20 minutes after the fabric was placed in the detergent solution, washing was stopped and the washed fabric was immediately removed from the detergent solution and rinsed for 30 seconds with cold tap water (13–15° C.). The wet fabric was centrifuged and ironed to remove wrinkles and dried at the same time.

Measurement of Washing Performance

Each sample of the washed and dried fabric was examined for stain removal by remission measurements (lightness Y) between 460 and 700 nm using a Spectraflash 500 (Datacolor). A cut off filter was used to eliminate potential interference by contamination with UV-absorbing materials. The lightness value of each test cloth was measured 5× and an average calculated.

With increasing washing performance, the lightness of the fabric increases. Washing performance is thus defined as a difference in lightness, ΔY:

ΔY=Lightness of fabric after washing—Lightness of fabric before washing

Example 11

Effect of Concentration of Crosslinked Subtilisin Crystals on Washing Performance of Detergents Containing Them Washing performance of crosslinked enzyme crystals according to this invention was examined as a function of their concentration in the liquid detergent, using the materials described below.
Test fabric: EMPA (Eidgenössische Materialprüfungs und Forschungsanstalt, St. Gallen, Switzerland) #116 soiled with a combination of blood, milk and carbon black.
Liquid detergent: Ciba detergent #16.
Enzyme:—Crosslinked enzyme crystals; sample Altus IV (as described in Example 6)—Uncrosslinked enzyme (Alcalase).
Concentration of Enzyme in Liquid Detergent: enzyme concentrations were between 0.05 and 0.9 w % (dry matter weight). Table XIV provides further details.

TABLE XIV

| Enzyme | Weight of enzyme suspension (g) | | Dry matter weight of enzyme | Liquid Detergent Ciba #16 |
|---|---|---|---|---|
| w % | Alcalase | Altus IV | g | g |
| 0.05 | 0.106 |  | 0.0053 | 10 |
| 0.05 |  | 0.130 | 0.0056 | 10 |
| 0.1 | 0.207 |  | 0.0104 | 10 |
| 0.1 |  | 0.240 | 0.0104 | 10 |
| 0.3 | 0.599 |  | 0.0301 | 10 |
| 0.3 |  | 0.683 | 0.0297 | 10 |
| 0.5 | 0.492 |  | 0.0247 | 5 |
| 0.5 |  | 0.580 | 0.0252 | 5 |
| 0.9 | 0.886 |  | 0.0445 | 5 |
| 0.9 |  | 1.046 | 0.0455 | 5 |

Preparation of Liquid Detergent with Enzyme

Specific aliquots of the suspension of enzyme crystals (see Table XIV) were added to a flask and centrifuged to separate the crystals from the liquid. The liquid was discarded and the crystals were suspended and homogenized in the liquid detergent (for quantities see Table XIV). The resulting preparations were used in the washing tests.

Figure 2:
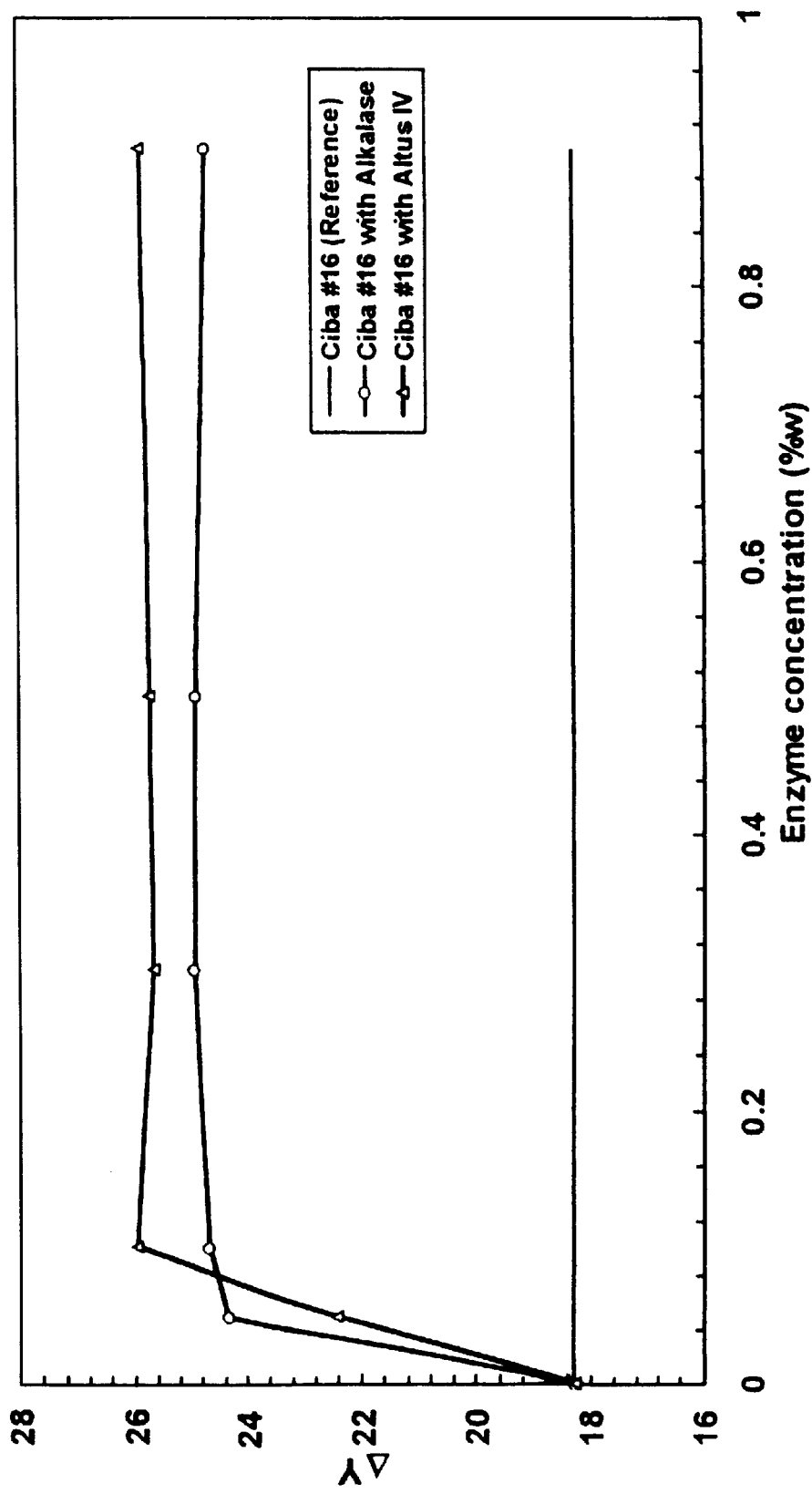
FIG. 2 is a graph representing the washing performance of liquid detergent formulations, including a formulation containing crosslinked subtilisin crystals according to the present invention, on fabric soiled with blood, milk and carbon black.

Washing tests to evaluate the performance of the enzyme detergent formulations were carried out as described in the assay above. The results of the study are depicted in FIG. 2. The figure demonstrates that at enzyme concentrations ≧0.1 w %, the washing effect of Ciba liquid detergent #16 formulated with Altus IV exceeds that of the formulation with uncrosslinked Alcalase. The efficacy of both crosslinked and uncrosslinked enzymes was reduced at enzyme concentrations below 0.1 w %.

Example 12

Figure 3:
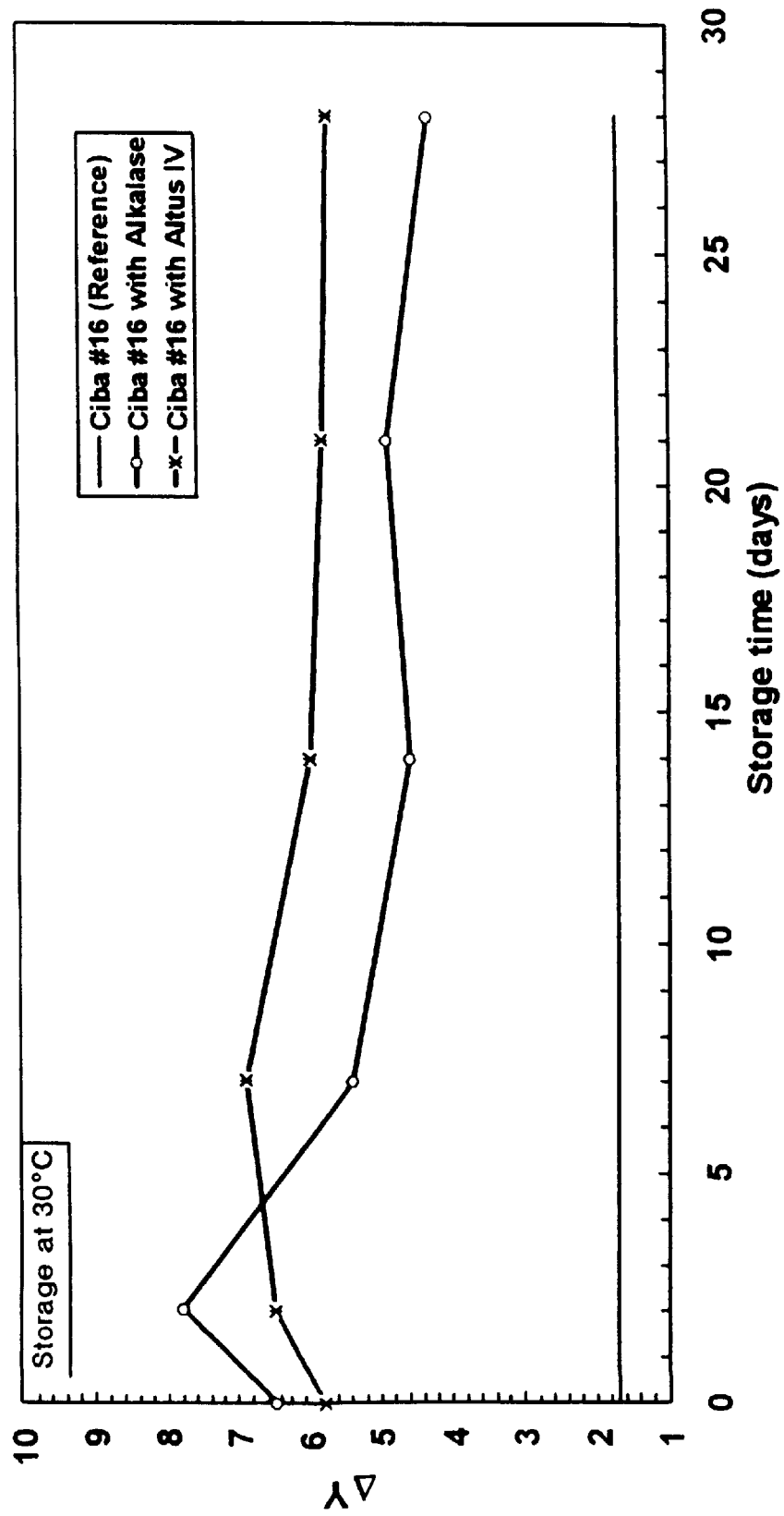
FIG. 3 is a graph representing the washing performance of liquid detergent formulations, including a formulation containing crosslinked subtilisin crystals according to the present invention, after storage at 30° C., on fabric soiled with cocoa.
Figure 4:
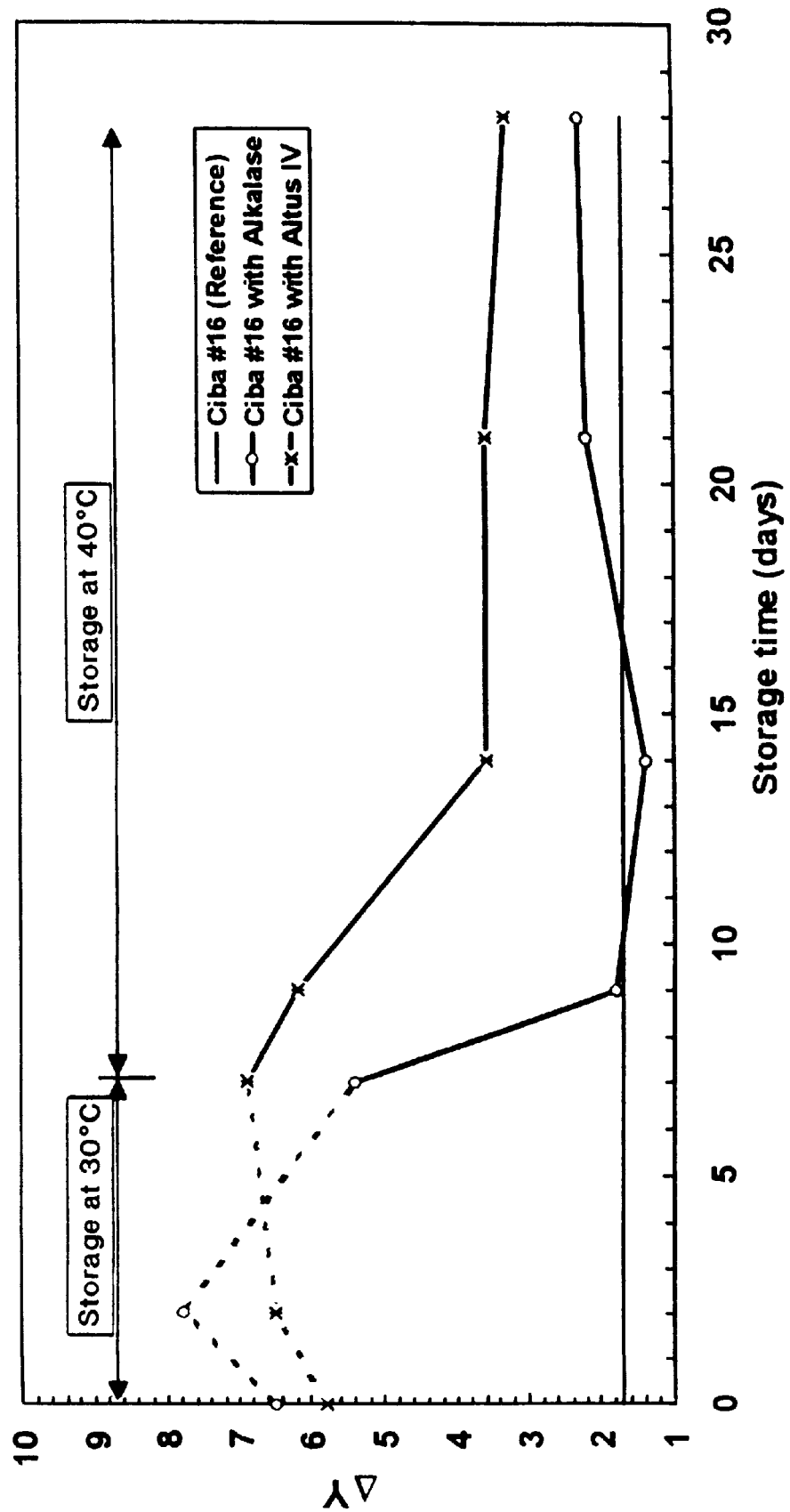
FIG. 4 is a graph representing the washing performance of liquid detergent formulations, including a formulation containing crosslinked subtilisin crystals according to the present invention, after storage at 40° C., on fabric soiled with cocoa.

Storage Stability and Washing Performance of Detergents Containing Crosslinked Subtilisin Crystals Detergents formulated with crosslinked and uncrosslinked enzymes were stored at a constant temperature, in order to examine enzyme stability in concentrated liquid detergent. The detergent formulations (150 g each) were prepared by the same procedure as the samples in Example 10.
Liquid detergent: Ciba detergent #16.
Enzyme:—Crosslinked enzyme crystals: sample Altus IV (Example 6)—Uncrosslinked enzyme (Alcalase)
Enzyme concentration: 0.3 w % (dry matter) in liquid detergent.
Storage Temperature for Stability Studies:
All samples were stored at 30° C. for between 0 and 7 days. After 7 days, the samples were divided after 7 days into two equal portions, in order to study stability at elevated temperature. One portion continued to be stored at 30° C., while the other was stored at 40° C.
Test Fabric:
Three different soiled fabrics were used. All of them were standard test materials available from EMPA:
EMPA #112: cocoa soiled fabric
EMPA #116: blood, milk and carbon black soiled fabric
EMPA #111: blood soiled fabric.
Washing Performance on Cocoa Soiled Fabric Washing performance of various enzyme formulated liquid detergents was studied with respect to removal of cocoa stains from a cocoa soiled test fabric, using the washing assay described above. Storage stability was determined by assessing washing performance periodically during the detergent storage time, thus monitoring the impact of storage temperature on enzyme performance in the liquid detergent. In this assay, the effectiveness of the liquid detergent decreases as enzyme stability degrades. The results of this assay, shown in FIGS. 3 and 4, are discussed below.
Storage Stability at 30° C.

As demonstrated in FIG. 3, both Alcalase and Altus IV formulated detergents exhibited an improved performance after 2 days of storage (compared to initial values). However, as storage time increased, the performance of the Alcalase formulation decreased continuously over time, while the Altus IV formulated detergent exhibited no degradation, even after 28 days of storage.
Storage Stability at 40° C.

As demonstrated in FIG. 4, when the temperature was raised from 30 to 40° C., Alcalase formulated detergent lost activity within 2 days, while the Altus IV formulated detergent degraded slightly, while removing the cocoa soil from the test fabric significantly, even after 21 days of storage at 40° C.
Washing Performance on Fabric Soiled by a Combination of Blood, Milk and Carbon Black (EMPA #116 test fabric)

Figure 5:
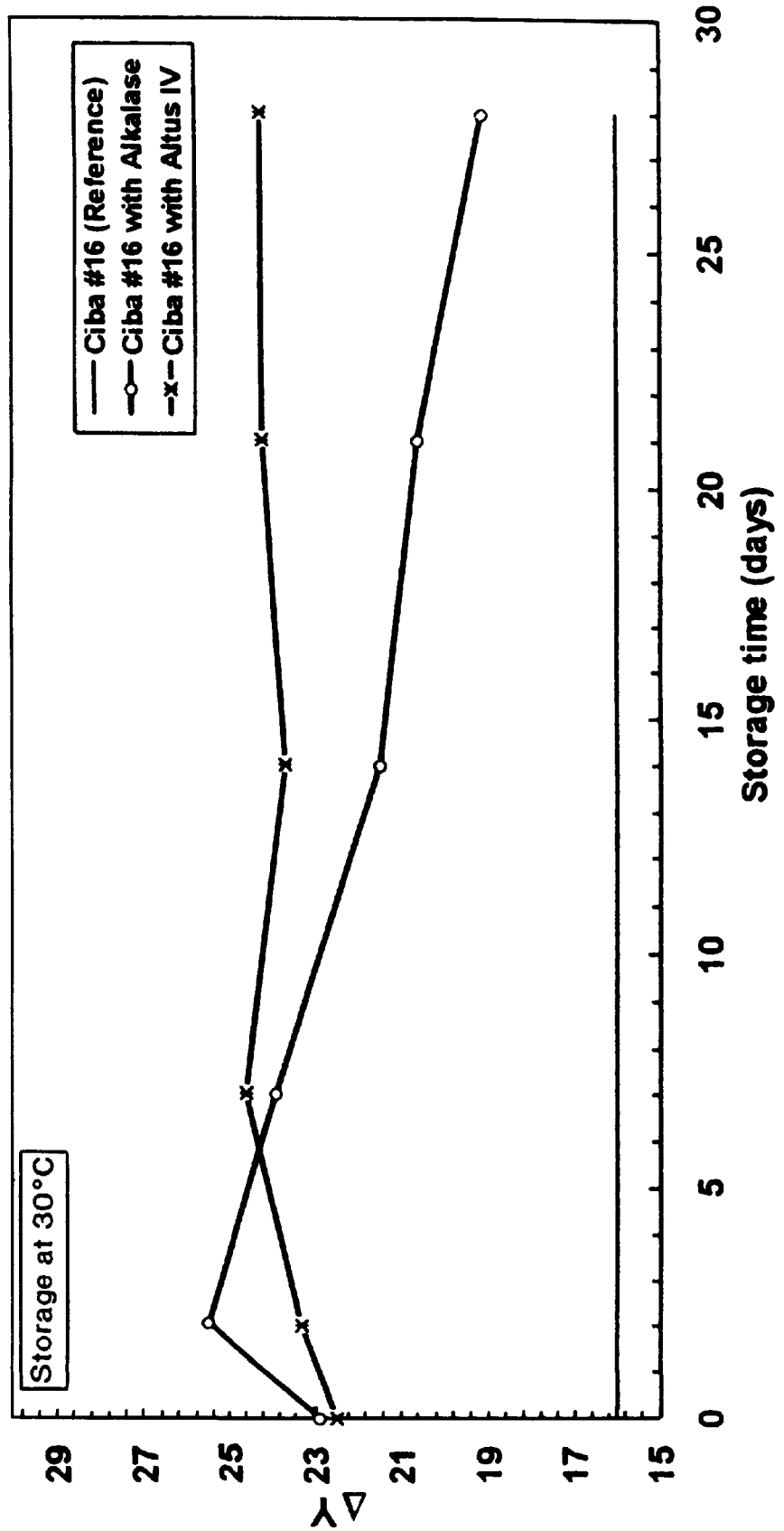
FIG. 5 is a graph representing the washing performance of liquid detergent formulations, including a formulation containing crosslinked subtilisin crystals according to the present invention, after storage at 30° C., on fabric soiled with blood, milk and carbon black.
Figure 6:
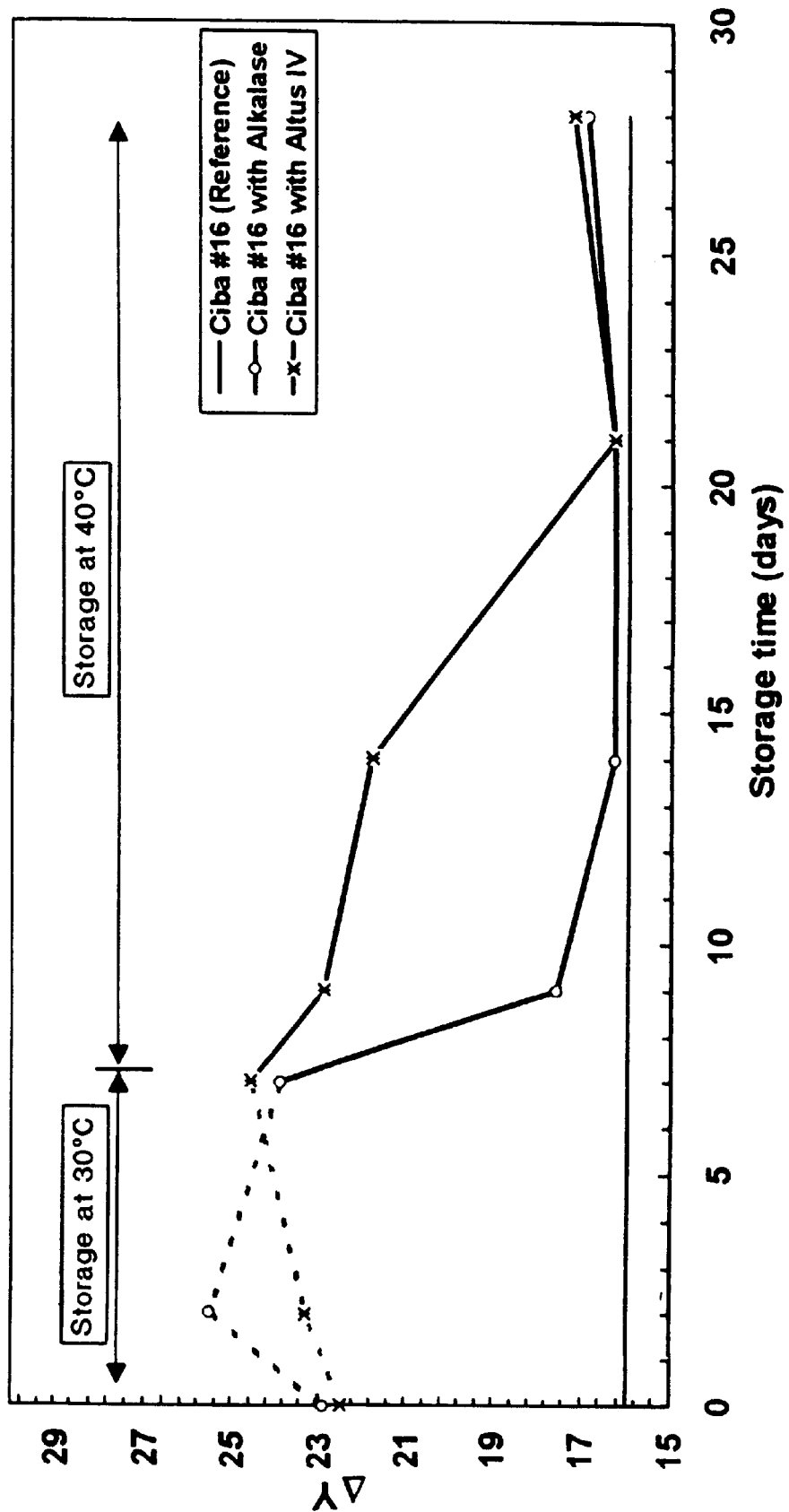
FIG. 6 is a graph representing the washing performance of liquid detergent formulations, including a formulation containing crosslinked subtilisin crystals according to the present invention, after storage at 40° C., on fabric soiled with blood, milk and carbon black.

The experimental conditions and detergents were the same (except the stained fabric) as for washing of cocoa stains. The results of the washing tests are depicted in FIGS. 5 and 6.
Storage Stability at 30° C.

FIG. 5 clearly illustrates the decay of washing performance of the Alcalase formulated detergent after 2 days of storage at 30° C. However, liquid detergent containing Altus IV enzyme maintained its original washing performance, even after 28 days of storage.
Storage Stability at 40° C.

Figure 7:
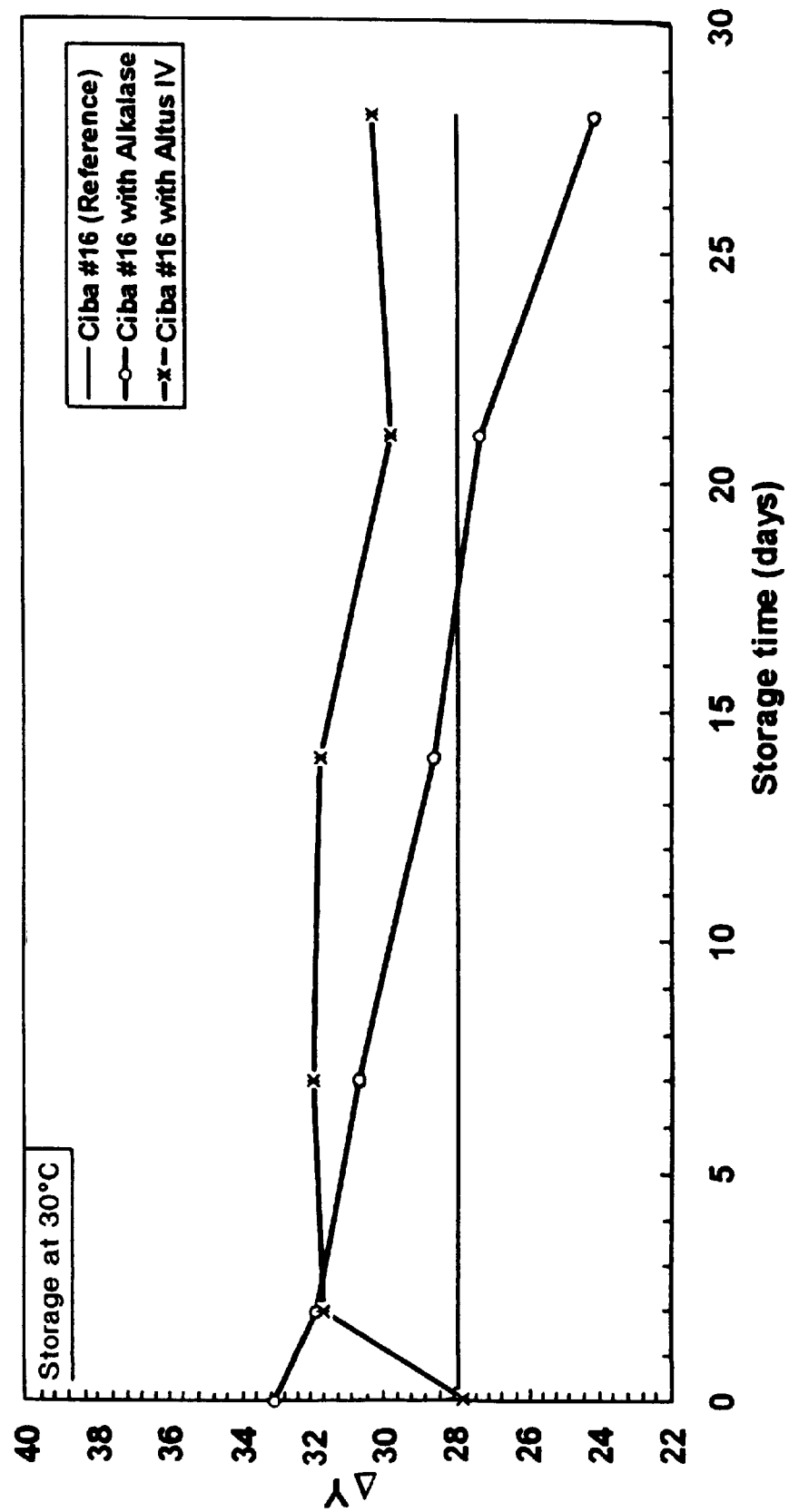
FIG. 7 is a graph representing the washing performance of liquid detergent formulations, including a formulation containing crosslinked subtilisin crystals according to the present invention, after storage at 30° C., on fabric soiled with blood.

As demonstrated in FIG. 6, when the storage temperature was raised from 30 to 40° C., Alcalase formulated detergent lost nearly all of its washing performance within 2 days. In contrast, detergent containing Altus IV retained its washing power for an additional 14 days.
Washing Performance on Fabric Soiled with Blood Washing performance on blood stains was tested with enzyme containing detergents stored at 30° C. The detergent composition, washing conditions were the same as in washing of cocoa stains. The results of the washing test are illustrated in FIG. 7.

The assays show that the washing effect on blood stain by Ciba #16 liquid detergent formulated with Alcalase was low in comparison to detergent without enzyme. On the other hand, the Altus IV formulation was more active in washing conditions and more stable in storage.

Storage Stability at 30° C.

The washing effect of Alcalase formulated detergent decreased rapidly with storage time, whereas Altus IV formulated detergent retained almost completely its full capacity after 28 days of storage.

Example 13

Solubility of Crosslinked Subtilisin Crystals at 30° C. and 37° C.

We studied the solubility of various subtilisin crystals, which had been crosslinked with glutaraldehyde (GA), octanedialdehyde (OA), neopentyl glycol diglycidyl ether (NP) followed by glutaraldehyde, or DENACOL EX-411 (411) followed by glutaraldehyde.

In 1.5 ml Eppendorf tubes, samples of uncrosslinked subtilisin crystals and crosslinked subtilisin crystal slurry, equal to 37.5 mg of enzyme, were microfuged at 5,000 rpm for 5 min and the supernatant liquid was removed. A 1.5 ml aliquot of PBS buffer (0.01 M phosphate, 0.0027 M potassium chloride, 0.137 M sodium chloride, pH 7.4) was added to each sample, bringing the concentration of subtilisin to 25 mg/ml. The samples were transferred to 2 ml glass vials with screw caps and magnetic stir bars then were incubated at 30° C. or at 37° C. Samples were studied for dissolution by periodically removing 50 µl of the slurry, microfuging at 13,000 rpm for 5 mins, removing 20 µl of the aliquot and placing it in 980 µl of deionized water, then measuring UV absorbance at 280 nm.

The following samples were studied:

| Crosslinker | Crosslinker Concentration | Crosslinking Time |
| --- | --- | --- |
| GA | 1.0% | 1.5 h |
| GA | 0.25% | 2 h |
| GA | 0.2% | 2 h |
| GA | 0.15% | 2 h |
| NP/GA | 0.1%/0.1% | 5 h/1.5 h |
| 411/GA | 0.015%/0.035% | 16 h/1 h |
| OA | 0.2% | 16 h |
| OA | 0.1% | 16 h |
| OA | 0.05% | 16 h |

Figure 8:
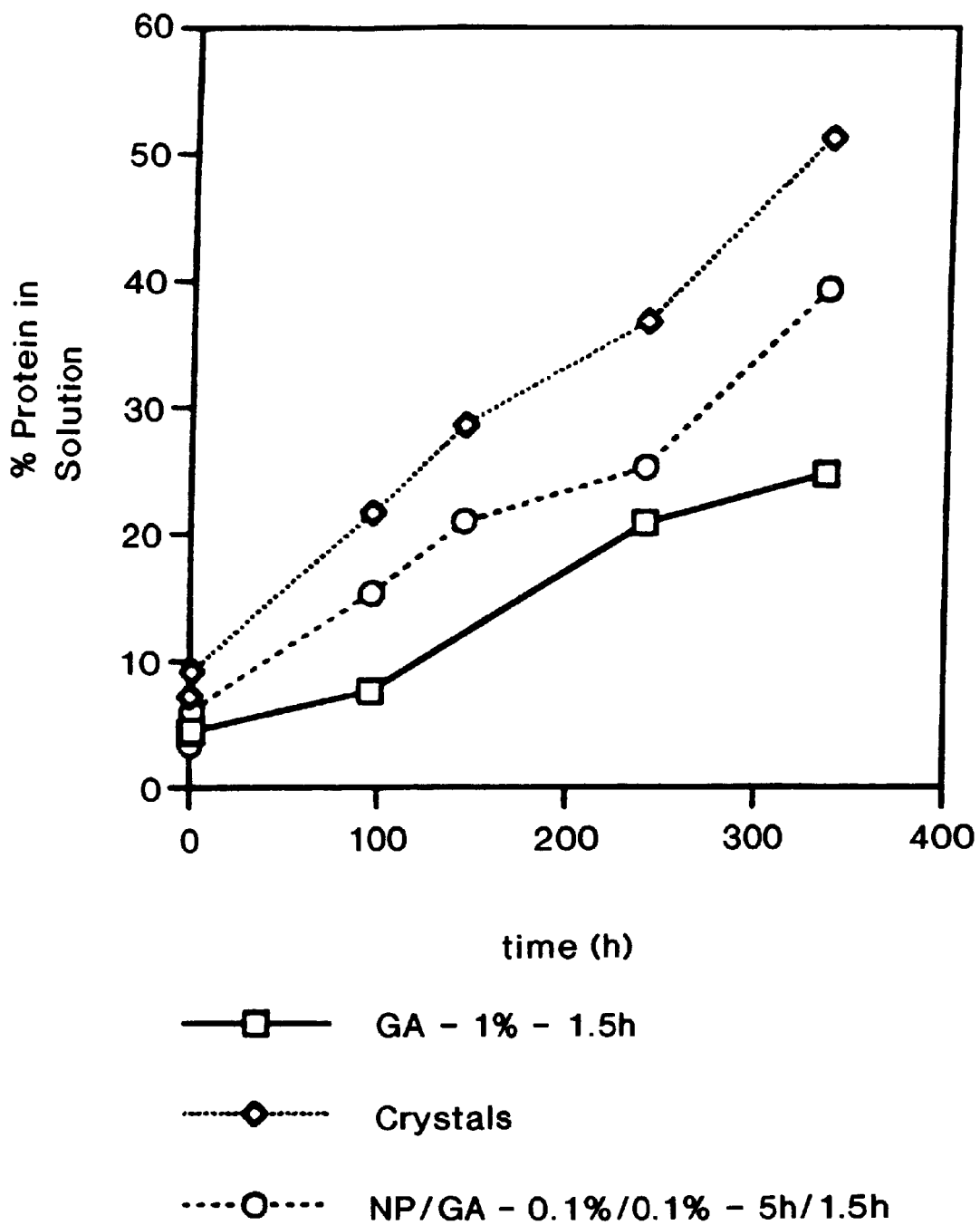
FIG. 8 is a graph representing the solubility of crosslinked subtilisin crystals according to the present invention at 30° C.
Figure 9:
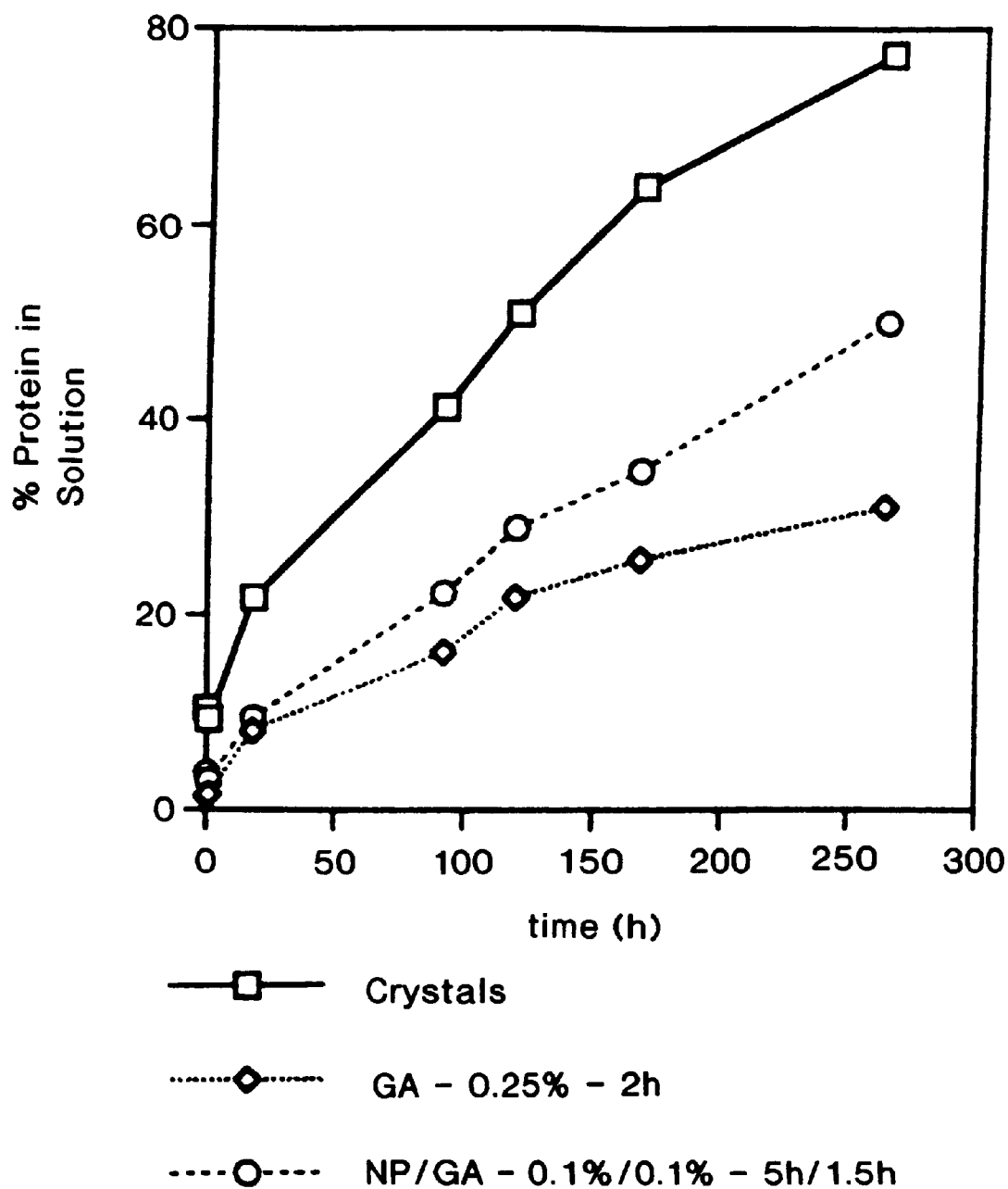
FIG. 9 is a graph representing the solubility of crosslinked subtilisin crystals according to the present invention at 37° C.

The solubility profiles of the samples, shown in FIGS. 8 and 9, illustrate different rates of dissolution for the crosslinked crystals.

Example 14

Reversible Crosslinkers—Disulfide Crosslinked Subtilisin Crystals

We prepared subtilisin crystals (30–40 µm average, 27 mg/ml in $Na_2SO_4$) as previously described for subtilisin crystallization.

We then crosslinked the crystals using one of the following crosslinkers:
1) Dimethyl 3,3'-dithiobispropionimidate•HCl—(DTBP) (Pierce)
2) Dithiobis(succinimidylpropionate)—(DSP) (Pierce)
3) 3,3'-Dithiobis(sulfosuccinimidylpropionate)—(DTSSP) (Pierce).

Crosslinking was carried out in 15 ml neoprene screw cap tubes by placing 740 µl of subtilisin crystal slurry (20 mg) in 9.26 ml of buffer (25 mM $NaCO_3$/50 mM $NaHCO_3$, pH 8.0). One crosslinker was added to each tube as follows: A) 93 mg DTBP (30 mM) B) 100 mg DTSSP (16 mM) C) 120 mg DSP (30 mM).

The tubes were tumbled at ambient temperature (24–26° C.) until all samples were determined to be insoluble in 32 mM NaOH (5 days)—100 µl sample in 300 µl NaOH. Uncrosslinked samples were readily soluble in 32 mM NaOH at the same concentrations. Crosslinking was stopped by the addition of 1 ml of 1 M Tris, pH 7.5. The samples were centrifuged at 3,000 rpm for 5 minutes, the supernatant removed and replaced by 5 ml of 100 mM Tris, pH 7.5. Centrifugation at 3,000 rpm, for 5 min, followed by replacement of supernatant with 5 ml of 100 mM Tris (pH 7.5) was repeated 3×.

Example 15

Dissolution of Disulfide Bond-Containing Crosslinked Subtilisin Crystals

A 200 mM solution of cysteine was prepared by dissolving 121 mg cysteine in 5 ml 100 mM Tris (pH 7.5). A 400 µl aliquot of the cysteine solution was added to 3×750 µl vials. A 400 µl aliquot of 100 mM Tris (pH 7.5) was added to another 3×750 µl vials. Each crosslinked sample (100 µl) was added to one vial containing cysteine and one vial without cysteine. All samples were incubated at 37° C. and monitored for dissolution of crosslinked enzyme crystals (direct visual and microscopic observation).

After incubation for 3 hrs at 37° C., the DTBP sample appeared to be fully soluble in the presence of cysteine and insoluble in its absence. The DTSSP sample appeared to be nearly fully soluble in the presence of cysteine and insoluble in its absence. The DSP sample was barely soluble in the presence of cysteine and insoluble in its absence.

Example 16

Crystallization of *Candida Rugosa* Lipase

A 5 kg aliquot of *Candida rugosa* lipase ("CRL") in powder form (Meito) was mixed with 5 kg celite and dissolved in 102 L distilled deionized water and the volume brought to 200 L with the deionized water. The suspension was mixed in an Air Drive Lightning Mixer for 2 hours at room temperature and then filtered through a 0.5 micron filter to remove celite. The mixture was then ultrafiltered and concentrated to 14 L (469 g) using a 3K hollow fiber filter membrane cartridge. Solid calcium acetate was added to a concentration of 5 mM $Ca(CH_3COO)_2$. The pH was adjusted to pH 5.5 with concentrated acetic acid as necessary. A 7 litre aliquot was crystallized by either addition of 1.75 litres of 2-methyl-2,4-pentanediol ("MPD") or by addition of 3.5 litres of a 30% solution of PEG-8000. The resulting solution was mixed and crystallization allowed to proceed overnight at ambient temperature for about 17–20 hrs. The crystal yield was about 70%.

Recrystallization

The *Candida rugosa* lipase crystals were solubilized by the addition of 50 mM sodium phosphate (pH 5.2). Soluble protein concentration of the crystallization solution was adjusted to 20 mg/ml. MPD was added gradually with stirring over a 6-hour period, to a final concentration of 25%. The resulting solution was mixed and crystallization allowed to proceed at ambient temperature for 20 hours.

Example 17

Crystallization of Candida Rugosa Lipase

Candida rugosa lipase crystals prepared as described in Example 16, prior to the solubilization and recrystallization steps, were solubilized by the addition of 50 mM sodium acetate (pH 6.5). Soluble protein concentration of the crystallization solution was adjusted to 20 mg/ml. MPD was added gradually with stirring over a 6-hour period to a final concentration of 20%. The resulting solution was mixed and crystallization allowed to proceed at ambient temperature for 20 hours.

Example 18

Crosslinking of Candida Rugosa Lipase Crystals

Candida rugosa lipase crystals, prepared as described in Example 16, were crosslinked by addition of untreated neat glutaraldehyde (Sigma) by adding 2 ml of 20% glutaraldehyde stepwise in a 40.5 ml volume over one hour to 8 ml of stirred lipase crystals (25 mg/ml), at ambient temperature. The final crosslinker concentration was 4.0%. Crosslinking was allowed to proceed over 24 hours. Crystals were recovered by low speed centrifugation and washed with 25% MPD in 50 mM sodium phosphate (pH 5.2).

Example 19

Crosslinking of Candida Rugosa Lipase Crystals

Candida rugosa lipase crystals, prepared as described in Example 16, were crosslinked by addition of untreated neat glutaraldehyde by adding 2 ml of 20% glutaraldehyde gradually over a one hour period. Crystals were crosslinked and processed as described in Example 18.

Example 20

Crosslinking of Candida Rugosa Lipase Crystals

Candida rugosa lipase crystals, prepared as described in Example 16, were crosslinked as described in in Example 19, except that the reaction was allowed to proceed for 24 hours. The crystals were then processed as described in Example 18.

Example 21

Crosslinking of Candida Rugosa Lipase Crystals

Candida rugosa lipase crystals, prepared as described in Example 17, were crosslinked by addition of glutaraldehyde to a final concentration of 4.0%. Crosslinking was allowed to proceed for 3 hours. The crystals were processed as described in Example 18.

Example 22

Crosslinking of Candida Rugosa Lipase Crystals

Candida rugosa lipase crystals, prepared as described in Example 17, were crosslinked in neat glutaraldehyde at a concentration of 6.5% for 1 hour. Crosslinking and processing were performed as described in Example 18.

Example 23

Crosslinking of Candida Rugosa Lipase Crystals

Candida rugosa lipase crystals, prepared as described in Example 17, were crosslinked in neat glutaraldehyde at a concentration of 6.0% for 1 hour. Crosslinking and processing were performed as described in Example 18.

Example 24 pH Controlled Solubility of Crosslinked Candida Rugosa Lipase Crystals

Solubility of various crosslinked Candida rugosa lipase crystals was studied following an increase in pH from 6.5 to 9.0. The crystals were incubated at 1 mg/ml in 50 mM sodium phosphate (pH 9) containing 25% MPD. Aliquots were removed after 3 hour and 24 hour incubation at 25° C. with stirring. Activity and soluble protein concentration were measured as described in Example 25. The results are described in the table below.

| | Crosslinked Crystal Preparation | | | |
|---|---|---|---|---|
| | Time (hr) | | | |
| | 3 | | 24 | |
| | Activity(U) | [Prot.] (mg/ml) | Activity(U) | [Prot.] (mg/ml) |
| Example 18 | 7.5 | 0.47 | 20 | 1 |
| Example 19 | 10.8 | 0.60 | 11.3 | 0.63 |
| Example 20 | 7.5 | 0.42 | 8.8 | 0.49 |

Example 25 pH Solubility of Crosslinked Candida Rugosa Lipase Crystals

Solubility of various crosslinked Candida rugosa lipase crystals was studied following an increase in pH from 5.2 to 7.5. The crystals were incubated at 1 mg/ml in 50 mM sodium phosphate (pH 7.5) containing 25% MPD. Aliquots were removed after 3 hour and 24 hour incubation at 25° C. with stirring. Insoluble material was removed by filtration (0.25 micron). Activity in solution was measured spectrophotometrically by monitoring the hydrolysis of para nitrophenyl acetate (Fluka) at 400 nm. Substrate concentration was 1 mM. The assay was performed at 25° C. in a 1 ml volume of 50 mM sodium acetate (pH 6.5). Soluble protein concentration was measured by absorbance at 280 mm. Results are presented in the table below.

| | Crosslinked Crystal Preparation | | | |
|---|---|---|---|---|
| | Time (hr) | | | |
| | 3 | | 24 | |
| | Activity(U) | [Prot.] (mg/ml) | Activity(U) | [Prot.] (mg/ml) |
| Example 21 | 2.4 | 0.12 | 15 | 0.91 |
| Example 22 | 10.0 | 0.63 | 15 | 1.0 |
| Example 23 | 2.5 | 0.17 | 11 | 0.69 |

Example 26

Crystallization of Human Serum Albumin

Human serum albumin ("HSA") was purchased from Sigma Chemical Company as a lyophilized powder. We added 10 grams of protein powder to a 75 ml stirred solution of 100 mM phosphate buffer pH 5.5 at 4° C. Final protein concentration was 120 mg/ml (determined from $OD_{280}$, extinction coefficient for serum albumin was assumed to equal 1). Saturated ammonium sulfate solution (767 g/l) prepared in deionized water was added to the protein solution to a final concentration of 50% saturation (350 g/l). The crystallization solution was "seeded" with 1 ml of albumin crystals (50 mg/ml) in 50% ammonium sulfate (pH 5.5). Seed crystals were prepared by washing a sample of crystals free of precipitate with a solution of 50% saturated ammonium sulfate in 100 mM phosphate buffer (pH 5.5). The seeded crystallization solution was incubated at 4° C. overnight on a vigorously rotating platform. Crystal rods (20µ) appeared in the solution overnight (16 hr).

Example 27

Crosslinking of Human Serum Albumin Crystals

We crosslinked human serum albumin crystals, prepared as described in Example 18, at 4° C. in a 10 ml stirred solution of crystals and mother liquor containing 50% saturated ammonium sulfate, as described above. The crystals, which were not washed prior to crosslinking, were crosslinked with glutaraldehyde as supplied by the manufacturer (Sigma). Glutaraldehyde ("GA") (20%) was added to the stirred crystallization solution in 4 equal volumes (62.5 µl) at 15 minute intervals to a final concentration of 0.5% (250 µl GA). The crystals were then incubated at 4° C. Aliquots were removed at incubation times 0, 30 min, 60 min and 4 hours incubation. Crosslinked albumin crystals were collected by low speed centrifugation and washed repeatedly with pH 7.5, 100 mM Tris HCl, 4° C. Washing was stopped when the crystals could be centrifuged at high speed without aggregation.

Example 28

Crosslinking of Human Serum Albumin Crystals

We crosslinked human serum albumin crystals as described in Example 27 above, with one modification; glutaraldehyde (20%) was added to the crystallization solution in 4 equal volumes (131.3 µl) at 15 minute intervals to a final concentration of 1% (525 µl GA).

Example 29

Solubility of Human Serum Albumin Crystals Crosslinked in 0.5% GA, time: 0 Minutes Incubation. Dissolution Induced by Elevated Temperature Human serum albumin, crystallized as described in Example 26 and crosslinked for 0 minutes in 0.5% glutaraldehyde, as described in Example 27, was assayed for solubility by incubating the crystals (20 mg/ml) with stirring, in phosphate buffered saline solution (pH 7.5) at room temperature ("RT") or at 37° C. Aliquots were removed for assay at times 0.5, 1, 4 and 24 hours. Insoluble material was removed from the solution by centrifugation and the soluble protein concentration was measured spectrophotometrically at 280 nm, as indicated in Table XV.

TABLE XV

| | Soluble Protein (mg/ml) | |
|---|---|---|
| Time (hr) | RT | 37° C. |
| 0.5 | 0.3 | 1.5 |
| 1.0 | 3 | 5 |
| 4.0 | 4 | 12.5 |
| 24.0 | 17 | 18.5 |

Example 30

Solubility of Human Serum Albumin Crystals Crosslinked in 0.5% GA, Time: 30 Minutes Incubation. Dissolution Induced by Elevated Temperature Human serum albumin, crystallized as described in Example 26 and crosslinked in 0.5% glutaraldehyde, as described in Example 27, was assayed for solubility by incubating the crystals (20 mg/ml) in phosphate buffered saline solution (pH 7.5) at room temperature or at 37° C. Aliquots were removed for assay at times 0.5, 1, 4 and 24 hours. Insoluble material was removed from the solution by centrifugation and the soluble protein concentration was measured spectrophotometrically at 280 nm, as indicated in Table XVI.

TABLE XVI

| | Soluble Protein (mg/ml) | |
|---|---|---|
| Time (hr) | RT | 37° C. |
| 0.5 | 1.5 | 4 |
| 1.0 | 3 | 5.5 |
| 4.0 | 7 | 10 |
| 24.0 | 13.5 | 17.5 |

Example 31

Solubility of Human Serum Albumin Crystals Crosslinked in 0.5% GA, Time: 60 Minutes Incubation. Dissolution Induced by Elevated Temperature Human serum albumin, crystallized as described in Example 26 and crosslinked with 0.5% glutaraldehyde, as described in Example 27, was assayed for solubility by incubating the crystals (20 mg/ml) in phosphate buffered saline solution (pH 7.5) at room temperature or at 37° C. Aliquots were removed for assay at times 0.5, 1, 4 and 24 hours. Insoluble material was removed from the solution by centrifugation and the soluble protein concentration was measured spectrophotometrically at 280 nm, as indicated in Table XVII.

TABLE XVII

| | Soluble Protein (mg/ml) | |
|---|---|---|
| Time (hr) | RT | 37° C. |
| 0.5 | 0 | 0.4 |
| 1.0 | 0 | 0.6 |
| 4.0 | 0 | 3 |
| 24.0 | 8 | 17 |

Example 32

Solubility of Human Serum Albumin Crystals Crosslinked in 0.5% GA, Time: 240 Minutes Incubation. Dissolution Induced by Elevated Temperature Human serum albumin, crystallized as described in Example 26 and crosslinked with 0.5% glutaraldehyde, as described in Example 27, was assayed for solubility by incubating the crystals (20 mg/ml) in phosphate buffered saline solution (pH 7.5) at room temperature or at 37° C. Aliquots were removed for assay at times 0.5, 1, 4 and 24 hours. Insoluble material was removed from the solution by centrifugation and the soluble protein concentration was measured spectrophotometrically at 280 nm, as indicated in Table XVIII.

TABLE XVIII

| Time (hr) | Soluble Protein (mg/ml) | |
| --- | --- | --- |
|  | RT | 37° C. |
| 0.5 | 0 | 0 |
| 1.0 | 0.5 | 0 |
| 4.0 | 3.5 | 3 |
| 24.0 | 8.5 | 14.5 |

Example 33

Solubility of Human Serum Albumin Crystals Crosslinked in 1.0% GA, Time: 0 Minutes Incubation. Dissolution Induced by Elevated Temperature Human serum albumin, crystallized as described in Example 26 and crosslinked as described in Example 27, was assayed for solubility by incubating the crystals (20 mg/ml) in phosphate buffered saline solution (pH 7.5) at room temperature or at 37° C. Aliquots were removed for assay at times 0.5, 1, 4 and 24 hours. Insoluble material was removed from the solution by centrifugation and the soluble protein concentration was measured spectrophotometrically at 280 nm, as indicated in Table XIX.

TABLE XIX

| Time (hr) | Soluble Protein (mg/ml) | |
| --- | --- | --- |
|  | RT | 37° C. |
| 0.5 | 1 | 2 |
| 1.0 | 3 | 7 |
| 4.0 | 10.5 | 16 |
| 24.0 | 19 | 18.5 |

Example 34

Solubility of Human Serum Albumin Crystals Crosslinked in 1.0% GA, Time: 30 Minutes Incubation. Dissolution Induced by Elevated Temperature Human serum albumin, crystallized as described in Example 26 and crosslinked as described in Example 27, was assayed for solubility by incubating the crystals (20 mg/ml) in phosphate buffered saline solution (pH 7.5) at room temperature or at 37° C. Aliquots were removed for assay at times 0.5, 1, 4 and 24 hours. Insoluble material was removed from the solution by centrifugation and the soluble protein concentration was measured spectrophotometrically at 280 nm, as indicated in Table XX.

TABLE XX

| Time (hr) | Soluble Protein (mg/ml) | |
| --- | --- | --- |
|  | RT | 37° C. |
| 0.5 | 0 | 0 |
| 1.0 | 0 | 2 |
| 4.0 | 4.5 | 7 |
| 24.0 | 8 | 13 |

Example 35

Solubility of Human Serum Albumin Crystals Crosslinked in 1.0% GA, Time: 60 Minutes Incubation. Dissolution Induced by Elevated Temperature Human serum albumin, crystallized as described in Example 26 and crosslinked as described in Example 27, was assayed for solubility by incubating the crystals (20 mg/ml) in phosphate buffered saline solution (pH 7.5) at room temperature or at 37° C. Aliquots were removed for assay at times 0.5, 1, 4 and 24 hours. Insoluble material was removed from the solution by centrifugation and the soluble protein concentration was measured spectrophotometrically at 280 nm, as indicated in Table XXI.

TABLE XXI

| Time (hr) | Soluble Protein (mg/ml) | |
| --- | --- | --- |
|  | RT | 37° C. |
| 0.5 | 0 | 0.5 |
| 1.0 | 0 | 1.5 |
| 4.0 | 1 | 4 |
| 24.0 | 9 | 13.5 |

Example 35

Solubility of Human Serum Albumin Crystals Crosslinked in 1.0% GA, Time: 240 Minutes Incubation. Dissolution Induced by Elevated Temperature Human serum albumin, crystallized as described in Example 26 and crosslinked as described in Example 27, was assayed for solubility by incubating the crystals (20 mg/ml) in phosphate buffered saline solution (pH 7.5) at room temperature or at 37° C. Aliquots were removed for assay at times 0.5, 1, 4 and 24 hours. Insoluble material was removed from the solution by centrifugation and the soluble protein concentration was measured spectrophotometrically at 280 nm, as indicated in Table XXII.

TABLE XXII

| Time (hr) | Soluble Protein (mg/ml) | |
| --- | --- | --- |
|  | RT | 37° C. |
| 0.5 | 0 | 0 |
| 1.0 | 0 | 0 |

TABLE XXII-continued

| | Soluble Protein (mg/ml) | |
|---|---|---|
| Time (hr) | RT | 37° C. |
| 4.0 | 0 | 2 |
| 24.0 | 6 | 10.3 |

Example 36

Crystallization of Thermolysin

Thermolysin was purchased from Diawa (Japan) as a lyophilized powder. Fifteen grams of protein powder were added to a 100 ml stirred solution of 10 mM calcium acetate (pH 11) at ambient temperature. The pH was maintained at 11 by addition of 2 N NaOH, until the thermolysin was completely solubilized. The pH was then adjusted to pH 7.5 by addition of 2 N acetic acid. Crystallization was allowed to proceed overnight at 4° C. Final protein concentration was 40 mg/ml (determined from $OD_{280}$, extinction coefficient for thermolysin was assumed to equal 1.8). Crystals were recovered by centrifugation and recrystallized to obtain a more uniform crystal size. Recrystallization was performed in a manner nearly identical to that described for the initial crystallization. Crystals (40 mg/ml protein) were dissolved by addition of base at room temperature. The pH of the crystallization solution was adjusted to 6.5 and crystallization was permitted to proceed at ambient temperature. Crystal rods (50μ) appeared in the solution overnight (16 hr).

Example 37

Crosslinking of Thermolysin Crystals

Thermolysin crystals, prepared as described in Example 36, were suspended (50 mg/ml) in a 50 mM solution of sodium acetate (pH 6.5). Crystals were crosslinked with glutaraldehyde as supplied by the manufacturer (Sigma). Ten milliliters of glutaraldehyde (10%) were added gradually over a 1 hour period with stirring to a 10 ml suspension of crystals. After all of the glutaraldehyde was added, the crystallization solution incubated at ambient temperature. Aliquots were removed at incubation times 0.5, 1 and 3 hr. Crosslinked crystals were collected by low speed centrifugation and washed exhaustively with pH 7.5 50 mM Tris HCl, containing 10 mM calcium acetate.

Example 38

Solubility of Thermolysin Crystals Crosslinked for 0.5 hr. Dissolution Induced by Removal of Calcium Ions by EDTA Thermolysin, crystallized as described in Example 36 and crosslinked for 0.5 hr as described in Example 37, was assayed for solubility by incubating the crystals (1 mg/ml) with stirring, in 10 mM Tris HCl (pH 7.2) containing 1 mM EDTA (Sigma) 40° C. One ml aliquots were removed for assay at times 0.5, 3 and 24 hours. Insoluble crystals were removed from the solution by filtration. One ml of 500 mM calcium acetate (pH 7.2) was added to each aliquot. Soluble protein concentration was measured spectrophotometrically at 280 nm. Enzymatic activity was measured spectrophotometrically by monitoring the hydrolysis of a dipeptide substrate, FAGLA (Feder). Substrate concentration was 1.67 mM. One unit is defined as the amount of enzyme required to hydrolyze 1 μmole of substrate in one minute at pH 7.2, 40° C. The activity of soluble thermolysin was 27 U/mg protein. Data is presented in Table XXIII.

TABLE XXIII

| Time (hr) | Soluble Protein (% of Max) | Activity (% of Max) |
|---|---|---|
| 0.5 | 80 | 30 |
| 3.0 | 103 | 97 |
| 24.0 | 100 | 91 |

Example 39

Solubility of Thermolysin Crystals Crosslinked for 1 hr. Dissolution Induced by Removal of Calcium Ions by EDTA Thermolysin, crystallized as described in Example 36 and crosslinked for 1 hr as described in Example 37, was assayed for solubility by incubating the crystals (1 mg/ml) with stirring, in 10 mM TrisHCl (pH 7.2) containing 1 mM EDTA 40° C. One ml aliquots were removed for assay at times 0.5, 3 and 24 hours. Insoluble crystals were removed from the solution by filtration. One ml of 500 mM calcium acetate (pH 7.2) was added to each aliquot. Soluble protein concentration was measured spectrophotometrically at 280 nm. Enzymatic activity was measured spectrophotometrically by monitoring the hydrolysis of a dipeptide substrate, FAGLA (Feder). Substrate concentration was 1.67 mM. One unit is defined as the amount of enzyme required to hydrolyze 1 μmole of substrate in one minute at pH 7.2, 40° C. The activity of soluble thermolysin was 27 U/mg protein. Data is presented in Table XXIV.

TABLE XXIV

| Time (hr) | Soluble Protein (% of Max) | Activity (% of Max) |
|---|---|---|
| 0.5 | 7 | 11 |
| 3.0 | 24 | 29 |
| 24.0 | 104 | 87 |

Example 40

Solubility of Thermolysin Crystals Crosslinked for 3 hr. Dissolution Induced by Removal of Calcium Ions by EDTA Thermolysin, crystallized as described in Example 36 and crosslinked for 3 hr as described in Example 37, was assayed for solubility by incubating the crystals (1 mg/ml) with stirring, in 10 mM TrisHCl (pH 7.2) containing 1 mM EDTA 40° C. One ml aliquots were removed for assay at times 0.5, 3 and 24 hours. Insoluble crystals were removed from the solution by filtration. One ml of 500 mM calcium acetate (pH 7.2) was added to each aliquot. Soluble protein concentration was measured spectrophotometrically at 280 nm. Enzymatic activity was measured spectrophotometrically by monitoring the hydrolysis of a dipeptide substrate, FAGLA (Feder). Substrate concentration was 1.67 mM. One unit is defined as the amount of enzyme required to hydrolyze 1 μmole of substrate in one minute at pH 7.2, 40° C. The activity of soluble thermolysin was 27 U/mg protein. Data is presented in Table XXV.

TABLE XXV

| Time (hr) | Soluble Protein (% of Max) | Activity (% of Max) |
|---|---|---|
| 0.5 | 2 | 0 |
| 3.0 | 2 | 0 |
| 24.0 | 100 | 73 |

Example 41

Solubility of Thermolysin Crystals Crosslinked for 3 hr. Dissolution Induced by Removal of Calcium Ions by Dilution Thermolysin crystals, prepared as described in Example 36 and crosslinked for 3 hr as described in Example 37, were washed free of calcium containing buffer and assayed for solubility by incubating the crystals (1 mg/ml) with stirring in deionized water. One ml aliquots were removed for assay at times 0.5, 3 and 24 hours. Insoluble crystals were removed from the solution by filtration. One ml of 500 mM calcium acetate (pH 7.2) was added to each aliquot. Soluble protein concentration was measured spectrophotometrically at 280 nm. Enzymatic activity was measured spectrophotometrically by monitoring the hydrolysis of a dipeptide substrate, FAGLA (Feder). Substrate concentration was 1.67 mM. One unit is defined as the amount of enzyme required to hydrolyze 1 $\mu$mole of substrate in one minute at (pH 7.2), 40° C. The activity of soluble thermolysin was 27 U/mg protein. Data is presented in Table XXVI.

TABLE XXVI

| Time (hr) | Soluble Protein (% of Max) | Activity (% of Max) |
|---|---|---|
| 0.5 | 0 | 0 |
| 3.0 | 0 | 7 |
| 24.0 | 111 | 81 |

Example 42

Crystallization of Glucose Isomerase

Glucose isomerase ("GA") was supplied by Cultor (Finland) as a crystal slurry. The enzyme was recrystallized by solubilizing a 50 ml volume of the crystal slurry at 50° C. with stirring for 15 minutes. The solution was clarified by filtration and allowed to cool slowly at room temperature. Fifty micron crystals appeared within 5 hours. Crystals were recovered by low speed centrifugation and washed with 166 mM magnesium sulfate.

Example 43

Crosslinking of Glucose Isomerase Crystals

Five hundred milligrams of glucose isomerase crystals, prepared as described in Example 42, were suspended in a 50 ml solution of 166 mM magnesium sulfate. The crystals were crosslinked with glutaraldehyde as supplied by the manufacturer (Sigma). Five milliliters of glutaraldehyde (10%) were added gradually over a 1 hour period with stirring to the 50 ml suspension. After all of the glutaraldehyde was added, the crystallization solution incubated at ambient temperature. Aliquots were removed at incubation times 1, 3 and 24 hr. Crosslinked crystals were collected by low speed centrifugation and washed exhaustively with 50 mM Tris HCl (pH 7.0).

Example 44

Solubility of Glucose Isomerase Crystals Crosslinked for 1 hr. Dissolution Induced by Removal of Calcium Ions by Dilution at 50° C.

Glucose isomerase crystals, prepared as described in Example 42 and crosslinked for 1 hr as described in Example 43 were, assayed for solubility by incubating the crystals (1 mg/ml) with stirring in deionized water. One ml aliquots were removed for assay at times 1, 3 and 24 hours. Soluble protein concentration was measured spectrophotometrically at 280 nm (OD280) (extinction coefficient for GI was assumed to equal 1). Enzymatic activity was measured spectrophotometrically by monitoring the conversion of fructose to glucose.

Glucose concentration was quantitated spectrophotometrically using a coupled enzyme assay containing hexokinase and glucose-6-phosphate dehydrogenase. The dehydrogenase uses NADP as a cofactor and the amount of NADPH formed in the reaction is stoichiometric with the concentration of substrate (glucose). The assay was purchased as a kit from Boehringer Mannheim and was used according to the manufacturer's instructions. One unit is defined as the amount of enzyme required to convert 1 $\mu$mole fructose to glucose in one minute at pH 7.0, 60° C. The activity of soluble glucose isomerase was 51 U/mg protein. Data is presented in Table XXVII.

TABLE XXVII

| Time (hr) | Soluble Protein (% of Max) | Activity (% of Max) |
|---|---|---|
| 0.5 | 8 | 0 |
| 3.0 | 52 | 31 |
| 24.0 | 100 | 57 |

Example 45

Solubility of Glucose Isomerase Crystals Crosslinked for 3 hr. Dissolution Induced by Removal of Calcium Ions by Dilution at 50° C.

Glucose isomerase crystals, prepared as described in Example 42 and crosslinked for 3 hr as described in Example 43, were assayed for solubility by incubating the crystals (1 mg/ml) with stirring in deionized water. One ml aliquots were removed for assay at times 1, 3 and 24 hours. Soluble protein concentration was measured spectrophotometrically at 280 nm (OD280) (extinction coefficient for GI was assumed to equal 1). Enzymatic activity was measured spectrophotometrically by monitoring the conversion of fructose to glucose.

Glucose concentration was quantitated spectrophotometrically using the coupled enzyme assay containing hexokinase and glucose-6-phosphate dehydrogenase, as described in Example 44. Data is presented in Table XXVIII.

TABLE XXVIII

| Time (hr) | Soluble Protein (% of Max) | Activity (% of Max) |
|---|---|---|
| 0.5 | 2 | 0 |
| 3.0 | 10 | 6.5 |
| 24.0 | 86 | 43 |

Example 46

Solubility of Glucose Isomerase Crystals Crosslinked for 24 hr. Dissolution Induced by Removal of Calcium Ions by Dilution at 50° C.

Glucose isomerase crystals, prepared as described in Example 42 and crosslinked for 1 hr as described in Example 43, were assayed for solubility by incubating the crystals (1 mg/ml) with stirring in deionized water. One ml aliquots were removed for assay at times 1, 3 and 24 hours. Soluble protein concentration was measured spectrophotometrically at 280 nm (OD280) (extinction coefficient for glucose isomerase was assumed to equal 1). Enzymatic activity was measured spectrophotometrically by monitoring the conversion of fructose to glucose.

Glucose concentration was quantitated spectrophotometrically using the coupled enzyme assay containing hexokinase and glucose-6-phosphate dehydrogenase, as described in Example 44. Data is presented in Table XXIX.

TABLE XXIX

| Time (hr) | Soluble Protein (% of Max) | Activity (% of Max) |
|---|---|---|
| 0.5 | 2 | 0 |
| 3.0 | 24 | 5 |
| 24.0 | 83 | 61 |

Example 47

Preparation of Tablets Containing Crosslinked Protein Crystals According to this Invention Tablets containing crosslinked protein crystals according to this invention may be prepared as follows. A suspension of crosslinked protein crystals is placed in 0.1 M sodium acetate, 20 mM calcium chloride and buffer (pH 7) and dried at 35° C. The resulting dried material may be mixed with sorbitol 50:50 by weight and granulated with Eudragit NE 30D (a neutral copolymer based on ethyl- and methylacrylate) or Eudagit RL 30D (an ammoniomethacrylate copolymer). The granules are dried (for example, for 16 hours at 40° C.) and compressed to round tablets of about 5 mm diameter and weight of about 125 mg. The content of crosslinked protein crystals in such solid preparations is about 45% by weight. If the above-described preparation is made without using sorbitol, the resulting tablets contain about 63% by weight crosslinked protein crystals.

When introduced into water or aqueous buffer (such as the above-described acetate buffer) all the tablets disintegrate in a matter of 10 minutes under mild shaking at room temperature) producing particles less than 100 $\mu$m in size, the majority in the range of 4–10 $\mu$m. Microscopic examination reveals polymer-free singular protein crystals, as the predominant species. The slurry obtained by disrupting the tablets is assayed titrimetrically using hydrolysis of N($\alpha$)-p-tosyl L-arginine methyl ester (TAME) at 25° C. (pH 8). Activity corresponding to between about 50% and 80% of activity of an equal amount of crosslinked protein crystals (counting the indicated weight of the crosslinked crystals, rather than of the whole tablets) results.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

What is claimed is:

1. A method for producing crosslinked protein crystals crosslinked with a multifunctional crosslinking agent, comprising the step of reacting a slurry of protein crystals with a multifunctional crosslinking agent, under conditions sufficient to induce crosslinking of said crystals to the extent that the resulting crosslinked crystals are characterized by the ability to change from insoluble and stable form to soluble and active form upon a change in their environment, said change being selected from the group consisting of change in temperature, change in pH, change in chemical composition, change from concentrate to dilute form, change in shear force acting upon the crystals and combinations thereof;

wherein said multifunctional crosslinking agent is glutaraldehyde and the concentration of said glutaraldehyde is between about 0.0076% and about 0.5% (vol/vol) based on the volume of said slurry of protein crystals to be crosslinked and wherein the conditions sufficient to induce crosslinking include reacting said protein crystals with said glutaraldehyde for a period of time between about 3 minutes and about 120 minutes.

2. A method for producing crosslinked protein crystals crosslinked with a multifunctional crosslinking agent, comprising the step of reacting a slurry of protein crystals with a multifunctional crosslinking agent, under conditions sufficient to induce crosslinking of said crystals to the extent that the resulting crosslinked crystals are characterized by a half-life of activity under storage conditions which is greater than at least 2 times that of the soluble form of the protein that is crystallized to form said crystals that are crosslinked, and by an activity similar to that of the soluble form of the protein under conditions of use;

wherein said multifunctional crosslinking agent is glutaraldehyde and the concentration of said glutaraldehyde is between about 0.0076% and about 0.5% (vol/vol) based on the volume of said slurry of protein crystals to be crosslinked and wherein the conditions sufficient to induce crosslinking include reacting said protein crystals with said glutaraldehyde for a period of time between about 3 minutes and about 120 minutes.

3. A method for producing crosslinked protein crystals crosslinked with a multifunctional crosslinking agent, comprising the step of reacting a slurry of protein crystals with a multifunctional crosslinking agent, under conditions sufficient to induce crosslinking of said crystals to the extent that the resulting crosslinked crystals are characterized by being capable of releasing their protein activity at a controlled rate upon exposure to a change in their environment, said change being selected from the group consisting of change in pH, change in soluble concentration, change in temperature, change in chemical composition, change in shear force acting upon the crystals and combinations thereof;

wherein said multifunctional crosslinking agent is glutaraldehyde and the concentration of said glutaraldehyde is between about 0.0076% and about 0.5% (vol/vol) based on the volume of said slurry of protein crystals to be crosslinked and wherein the conditions sufficient to induce crosslinking include reacting said protein crystals with said glutaraldehyde for a period of time between about 3 minutes and about 120 minutes.

4. The method for producing crosslinked protein crystals according to any one of claims 1, 2 or 3, wherein the concentration of said glutaraldehyde is about 0.005% (vol/vol) based on the volume of said slurry of protein crystals to be crosslinked and wherein the conditions sufficient to induce crosslinking include reacting said protein crystals with said glutaraldehyde for a period of time between about 10 minutes and about 30 minutes.

5. The method for producing crosslinked protein crystals according to any one of claims 1, 2 or 3, wherein, prior to reaction with said protein crystals, said glutaraldehyde is pretreated by incubation at 60° C. with a buffer for 1 hour.

6. A method for producing crosslinked protein crystals crosslinked with a multifunctional crosslinking agent, comprising the step of reacting a slurry of protein crystals with a multifunctional crosslinking agent, under conditions sufficient to induce crosslinking of said crystals to the extent that the resulting crosslinked crystals are characterized by the ability to change from insoluble and stable form to soluble and active form upon a change in their environment, said change being selected from the group consisting of change in temperature, change in pH, change in chemical composition, change from concentrate to dilute form, change in shear force acting upon the crystals and combinations thereof;

wherein said multifunctional crosslinking agent is glyoxal and the concentration of glyoxal is between about 0.01% and about 1% (vol/vol) based on the volume of said slurry of protein crystals to be crosslinked and wherein the conditions sufficient to induce crosslinking include reacting said protein crystals with said glyoxal for a period of time between about 30 minutes and about 60 minutes.

7. A method for producing crosslinked protein crystals crosslinked with a multifunctional crosslinking agent, comprising the step of reacting a slurry of protein crystals with a multifunctional crosslinking agent, under conditions sufficient to induce crosslinking of said crystals to the extent that the resulting crosslinked crystals are characterized by a half-life of activity under storage conditions which is greater than at least 2 times that of the soluble form of the protein that is crystallized to form said crystals that are crosslinked, and by an activity similar to that of the soluble form of the protein under conditions of use;

wherein said multifunctional crosslinking agent is glyoxal and the concentration of glyoxal is between about 0.01% and about 1% (vol/vol) based on the volume of said slurry of protein crystals to be crosslinked and wherein the conditions sufficient to induce crosslinking include reacting said protein crystals with said glyoxal for a period of time between about 30 minutes and about 60 minutes.

8. A method for producing crosslinked protein crystals crosslinked with a multifunctional crosslinking agent, comprising the step of reacting a slurry of protein crystals with a multifunctional crosslinking agent, under conditions sufficient to induce crosslinking of said crystals to the extent that the resulting crosslinked crystals are characterized by being capable of releasing their protein activity at a controlled rate upon exposure to a change in their environment, said change being selected from the group consisting of change in pH, change in soluble concentration, change in temperature, change in chemical composition, change in shear force acting upon the crystals and combinations thereof;

wherein said multifunctional crosslinking agent is glyoxal and the concentration of glyoxal is between about 0.01% and about 1% (vol/vol) based on the volume of said slurry of protein crystals to be crosslinked and wherein the conditions sufficient to induce crosslinking include reacting said protein crystals with said glyoxal for a period of time between about 30 minutes and about 60 minutes.

9. A method for producing crosslinked protein crystals crosslinked with a multifunctional crosslinking agent, comprising the step of reacting a slurry of protein crystals with a multifunctional crosslinking agent, under conditions sufficient to induce crosslinking of said crystals to the extent that the resulting crosslinked crystals are characterized by the ability to change from insoluble and stable form to soluble and active form upon a change in their environment, said change being selected from the group consisting of change in temperature, change in pH, change in chemical composition, change from concentrate to dilute form, change in shear force acting upon the crystals and combinations thereof;

wherein said multifunctional crosslinking agent is octanedialdehyde and the concentration of octanedialdehyde is between about 0.05% and about 1% (vol/vol) based on the volume of said slurry of protein crystals to be crosslinked and wherein the conditions sufficient to induce crosslinking include reacting said protein crystals with said octanedialdehyde for a period of time between about 30 minutes and about 16 hours.

10. A method for producing crosslinked protein crystals crosslinked with a multifunctional crosslinking agent, comprising the step of reacting a slurry of protein crystals with a multifunctional crosslinking agent, under conditions sufficient to induce crosslinking of said crystals to the extent that the resulting crosslinked crystals are characterized by a half-life of activity under storage conditions which is greater than at least 2 times that of the soluble form of the protein that is crystallized to form said crystals that are crosslinked, and by an activity similar to that of the soluble form of the protein under conditions of use;

wherein said multifunctional crosslinking agent is octanedialdehyde and the concentration of octanedialdehyde is between about 0.05% and about 1% (vol/vol) based on the volume of said slurry of protein crystals to be crosslinked and wherein the conditions sufficient to induce crosslinking include reacting said protein crystals with said octanedialdehyde for a period of time between about 30 minutes and about 16 hours.

11. A method for producing crosslinked protein crystals crosslinked with a multifunctional crosslinking agent, comprising the step of reacting a slurry of protein crystals with a multifunctional crosslinking agent, under conditions sufficient to induce crosslinking of said crystals to the extent that the resulting crosslinked crystals are characterized by being capable of releasing their protein activity at a controlled rate upon exposure to a change in their environment, said change being selected from the group consisting of change in pH, change in soluble concentration, change in temperature, change in chemical composition, change in shear force acting upon the crystals and combinations thereof;

wherein said multifunctional crosslinking agent is octanedialdehyde and the concentration of octanedialdehyde is between about 0.05% and about 1% (vol/vol) based on the volume of said slurry of protein crystals to be crosslinked and wherein the conditions sufficient to induce crosslinking include reacting said protein crystals with said octanedialdehyde for a period of time between about 30 minutes and about 16 hours.

12. The method for producing crosslinked protein crystals according to any one of claims 9, 10 or 11, wherein the concentration of said octanedialdehyde is about 1% (vol/vol) based on the volume of said slurry of protein crystals to be crosslinked and wherein the conditions sufficient to induce crosslinking include reacting protein crystals with said octanedialdehyde for a period of time between about 1 hour and about 3 hours.

13. A method for producing crosslinked protein crystals crosslinked with a multifunctional crosslinking agent, comprising the step of reacting a slurry of protein crystals with a multifunctional crosslinking agent, under conditions sufficient to induce crosslinking of said crystals to the extent that the resulting crosslinked crystals are characterized by the ability to change from insoluble and stable form to soluble and active form upon a change in their environment, said change being selected from the group consisting of change in temperature, change in pH, change in chemical composition, change from concentrate to dilute form, change in shear force acting upon the crystals and combinations thereof;

wherein said multifunctional crosslinking agent is succinaldehyde and the concentration of succinaldehyde is about 1% (vol/vol) based on the volume of said slurry of protein crystals to be crosslinked and wherein the conditions sufficient to induce crosslinking include reacting said protein crystals with said succinaldehyde for a period of time between about 30 minutes and about 3 hours.

14. A method for producing crosslinked protein crystals crosslinked with a multifunctional crosslinking agent, comprising the step of reacting a slurry of protein crystals with a multifunctional crosslinking agent, under conditions sufficient to induce crosslinking of said crystals to the extent that the resulting crosslinked crystals are characterized by a half-life of activity under storage conditions which is greater than at least 2 times that of the soluble form of the protein that is crystallized to form said crystals that are crosslinked, and by an activity similar to that of the soluble form of the protein under conditions of use;

wherein said multifunctional crosslinking agent is succinaldehyde and the concentration of succinaldehyde is about 1% (vol/vol) based on the volume of said slurry of protein crystals to be crosslinked and wherein the conditions sufficient to induce crosslinking include reacting said protein crystals with said succinaldehyde for a period of time between about 30 minutes and about 3 hours.

15. A method for producing crosslinked protein crystals crosslinked with a multifunctional crosslinking agent, comprising the step of reacting a slurry of protein crystals with a multifunctional crosslinking agent, under conditions sufficient to induce crosslinking of said crystals to the extent that the resulting crosslinked crystals are characterized by being capable of releasing their protein activity at a controlled rate upon exposure to a change in their environment, said change being selected from the group consisting of change in pH, change in soluble concentration, change in temperature, change in chemical composition, change in shear force acting upon the crystals and combinations thereof;

wherein said multifunctional crosslinking agent is succinaldehyde and the concentration of succinaldehyde is about 1% (vol/vol) based on the volume of said slurry of protein crystals to be crosslinked and wherein the conditions sufficient to induce crosslinking include reacting said protein crystals with said succinaldehyde for a period of time between about 30 minutes and about 3 hours.

16. A method for producing crosslinked protein crystals crosslinked with a multifunctional crosslinking agent, comprising the step of reacting a slurry of protein crystals with a first multifunctional crosslinking agent and at least a second multifunctional crosslinking agent, under conditions sufficient to induce crosslinking of said crystals to the extent that the resulting crosslinked crystals are characterized by the ability to change from insoluble and stable form to soluble and active form upon a change in their environment, said change being selected from the group consisting of change in temperature, change in pH, change in chemical composition, change from concentrate to dilute form, change in shear force acting upon the crystals and combinations thereof;

wherein said first multifunctional crosslinking agent is an epoxide and the concentration of epoxide is between about 0.01% and about 4% (vol/vol) based on the volume of said slurry of protein crystals to be crosslinked and said second multifunctional crosslinking agent is glutaraldehyde and the concentration of glutaraldehyde is between about 0.1% and about 0.2% (vol/vol) glutaraldehyde based on the volume of said slurry of protein crystals to be crosslinked and wherein the conditions sufficient to induce crosslinking include reacting said protein crystals with said epoxide for a period of time between about 1 hour and about 72 hours and reacting said protein crystals with said glutaraldehyde for a period of time between about 1 hour and about 5 hours.

17. A method for producing crosslinked protein crystals crosslinked with a multifunctional crosslinking agent, comprising the step of reacting a slurry of protein crystals with a first multifunctional crosslinking agent and at least a second multifunctional crosslinking agent, under conditions sufficient to induce crosslinking of said crystals to the extent that the resulting crosslinked crystals are characterized by a half-life of activity under storage conditions which is greater than at least 2 times that of the soluble form of the protein that is crystallized to form said crystals that are crosslinked, and by an activity similar to that of the soluble form of the protein under conditions of use;

wherein said first multifunctional crosslinking agent is an epoxide and the concentration of epoxide is between about 0.01% and about 4% (vol/vol) based on the volume of said slurry of protein crystals to be crosslinked and said second multifunctional crosslinking agent is glutaraldehyde and the concentration of glutaraldehyde is between about 0.1% and about 0.2% (vol/vol) glutaraldehyde based on the volume of said slurry of protein crystals to be crosslinked and wherein the conditions sufficient to induce crosslinking include reacting said protein crystals with said epoxide for a period of time between about 1 hour and about 72 hours and reacting said protein crystals with said glutaraldehyde for a period of time between about 1 hour and about 5 hours.

18. A method for producing crosslinked protein crystals crosslinked with a multifunctional crosslinking agent, comprising the step of reacting a slurry of protein crystals with a first multifunctional crosslinking agent and at least a second multifunctional crosslinking agent, under conditions sufficient to induce crosslinking of said crystals to the extent that the resulting crosslinked crystals are characterized by being capable of releasing their protein activity at a controlled rate upon exposure to a change in their environment, said change being selected from the group consisting of change in pH, change in soluble concentration, change in temperature, change in chemical composition, change in shear force acting upon the crystals and combinations thereof;

wherein said first multifunctional crosslinking agent is an epoxide and the concentration of epoxide is between about 0.01% and about 4% (vol/vol) based on the volume of said slurry of protein crystals to be crosslinked and said second multifunctional crosslinking agent is glutaraldehyde and the concentration of glutaraldehyde is between about 0.1% and about 0.2% (vol/vol) glutaraldehyde based on the volume of said slurry of protein crystals to be crosslinked and wherein the conditions sufficient to induce crosslinking include reacting said protein crystals with said epoxide for a period of time between about 1 hour and about 72 hours and reacting said protein crystals with said glutaraldehyde for a period of time between about 1 hour and about 5 hours.

19. The method for producing crosslinked protein crystals according to any one of claims 16, 17 or 18, wherein the concentration of said epoxide is about 0.01% (vol/vol) based on the volume of said slurry of protein crystals to be crosslinked and the concentration of said glutaraldehyde is about 0.1% (vol/vol) based on the volume of said slurry of protein crystals to be crosslinked and wherein the conditions sufficient to induce crosslinking include reacting said protein crystals with epoxide for about 5 hours and reacting said protein crystals with said glutaraldehyde for about 1.5 hours.

* * * * *

UNITED STATES PATENT AND TRADEMARK OFFICE
CERTIFICATE OF CORRECTION

PATENT NO.   : 6,140,475
DATED        : October 31, 2000
INVENTOR(S)  : Alexey L. Margolin et al.

Page 1 of 1

It is certified that error appears in the above-identified patent and that said Letters Patent is hereby corrected as shown below:

Column 1,
Line 44, change " ("CLEC$^{TM}$")" to -- (CLEC$^{TM}$) --.

Column 24,
Line 57, change first column head "90h" to -- 80h --.

Column 25,
Line 6, change first column head "90h" to -- 80h --.

Column 27,
Line 61, change "time" and "buffer" to -- Time -- and -- Buffer --.

Column 28,
Line 6, change "time" and "buffer" to -- Time -- and -- Buffer --.

Signed and Sealed this

Twenty-sixth Day of February, 2002

Attest:

*Attesting Officer*

JAMES E. ROGAN
*Director of the United States Patent and Trademark Office*